(12) United States Patent
Anderson et al.

(10) Patent No.: US 11,207,686 B2
(45) Date of Patent: Dec. 28, 2021

(54) MICROFLUIDIC DEVICE AND METHODS FOR DIGITAL ASSAYS IN BIOLOGICAL ANALYSES

(71) Applicant: Sharp Life Science (EU) Limited, Oxford (GB)

(72) Inventors: Sally Anderson, Oxford (GB); Pamela Ann Dothie, Oxford (GB); Philip Mark Shryane Roberts, Oxford (GB)

(73) Assignee: Sharp Life Science (EU) Limited, Oxford (GB)

( * ) Notice: Subject to any disclaimer, the term of this patent is extended or adjusted under 35 U.S.C. 154(b) by 335 days.

(21) Appl. No.: 16/107,320

(22) Filed: Aug. 21, 2018

(65) Prior Publication Data

US 2020/0061620 A1 Feb. 27, 2020

(51) Int. Cl.
*B01L 3/00* (2006.01)
*B01L 7/00* (2006.01)
*C12Q 1/6806* (2018.01)

(52) U.S. Cl.
CPC .......... *B01L 3/502784* (2013.01); *B01L 7/52* (2013.01); *B01L 2200/147* (2013.01); *B01L 2300/1805* (2013.01); *B01L 2400/0427* (2013.01); *C12Q 1/6806* (2013.01)

(58) Field of Classification Search
CPC ................ B01L 3/502784; B01L 7/52; B01L 2200/147; B01L 2300/1805; B01L 2400/0427; B01L 2300/1822; B01L 2200/0605; B01L 2200/0652; B01L 2300/0663; B01L 2300/1827;
(Continued)

(56) References Cited

U.S. PATENT DOCUMENTS

| 6,565,727 B1 | 5/2003 | Shenderov |
| 6,911,132 B2 | 6/2005 | Pamula et al. |
| 7,163,612 B2 | 1/2007 | Sterling et al. |

(Continued)

OTHER PUBLICATIONS

Gong et al. (J Gong, C-J Kim, All electronic droplet generation on-chip with real time feedback control for EWOD digital microfluidics, Lab Chip 8 (2008) 898-906) (Year: 2008).*

(Continued)

*Primary Examiner* — Joshua L Allen
(74) *Attorney, Agent, or Firm* — Renner, Otto, Boisselle & Sklar, LLP

(57) ABSTRACT

An EWOD device and a related method of performing a digital biological assay are described that employs two volume measurements for enhanced assay determination. The method includes partitioning a sample reservoir and measuring the volume of each partition; initiating a biological assay wherein the biological assay includes measuring a partition property and a volume of each partition in real time as part of determining a concentration of the product substance in each partition based on the measured partition property and volume; and categorizing the partitions by a number of biological entities contained in each partition from which the number of biological entities may be calculated, which in turn may be used to calculate the total number of biological entities or concentration in the sample reservoir. The method further may include an enhanced partitioning process that minimizes variation in the volume of the partitions.

25 Claims, 29 Drawing Sheets

(58) Field of Classification Search
CPC ......... B01L 3/502792; B01L 2300/161; C12Q 1/6806; C12Q 1/686; G01N 33/68
See application file for complete search history.

(56) References Cited

U.S. PATENT DOCUMENTS

| | | | |
|---|---|---|---|
| 8,137,917 B2 | 3/2012 | Pollack et al. | |
| 2010/0096266 A1* | 4/2010 | Kim | B01F 13/0076 204/451 |
| 2011/0268151 A1* | 11/2011 | Hadwen | B01L 3/502792 374/141 |
| 2013/0026040 A1* | 1/2013 | Cheng | B01L 3/502792 204/600 |
| 2016/0310949 A1* | 10/2016 | Kwang | B01L 3/502792 |
| 2016/0375437 A1* | 12/2016 | Hadwen | B01F 13/0071 204/451 |
| 2017/0059523 A1 | 3/2017 | Hadwen et al. | |

OTHER PUBLICATIONS

Schertzer et al. (MJ Schertzer, RB Mrad, PE Sullivan, Automated detection of particle concentration and chemical reactions in EWOD devices, Sensors and Actuators B 164 (2012) 1-6) (Year: 2012).*
Wijethunga et al. (PAL Wijethunga, YS Nanayakkara, P Kunchala, DW Armstrong, H Moon, On-chip drop-to-drop liquid microextraction coupled with real-time concentration monitoring technique, Anal. Chem. 83 (2011) 16585-1664) (Year: 2011).*
Fair, R.B., "Digital microfluids: is a true lab-on-a-chip possible?" Microfluidics and Nanofluidics Jun. 2007, vol. 3, Issue 3, pp. 245-281.
Nivedita Majumdar et al., "Poisson Plus Quantification for Digital PCR Systems" Scientific Reports Aug. 29, 2017, published online www.nature.com/scientificreports, pp. 1-10.
Lianhua Dong et al., "Comparison of four digital PCR platforms for accurate quantification of DNA copy number of a certified plasmid DNA reference material" Scientific Reports Aug. 25, 2015, published online www.nature.com/scientificreports, pp. 1-11.

* cited by examiner

Fig. 1: PRIOR ART

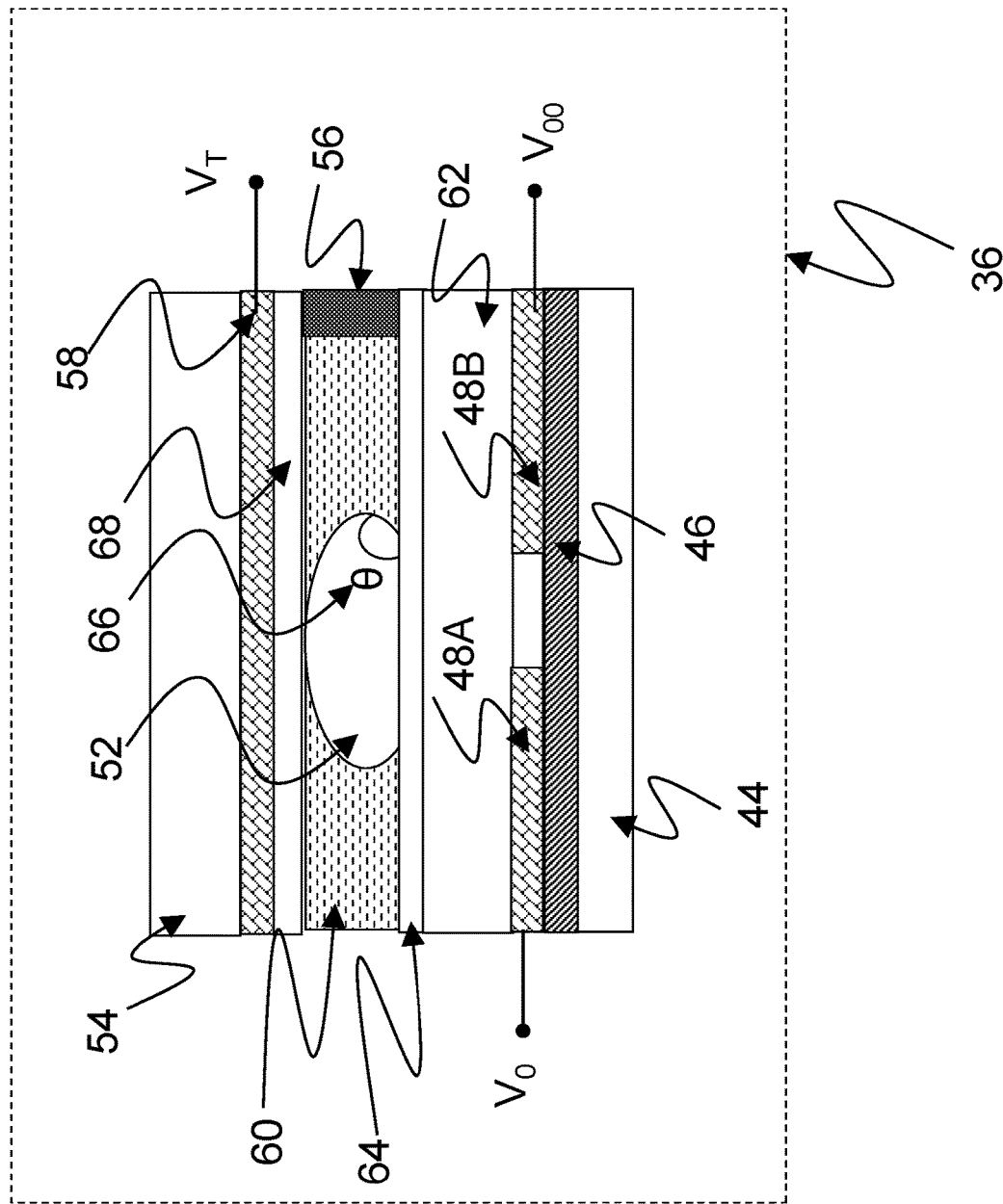

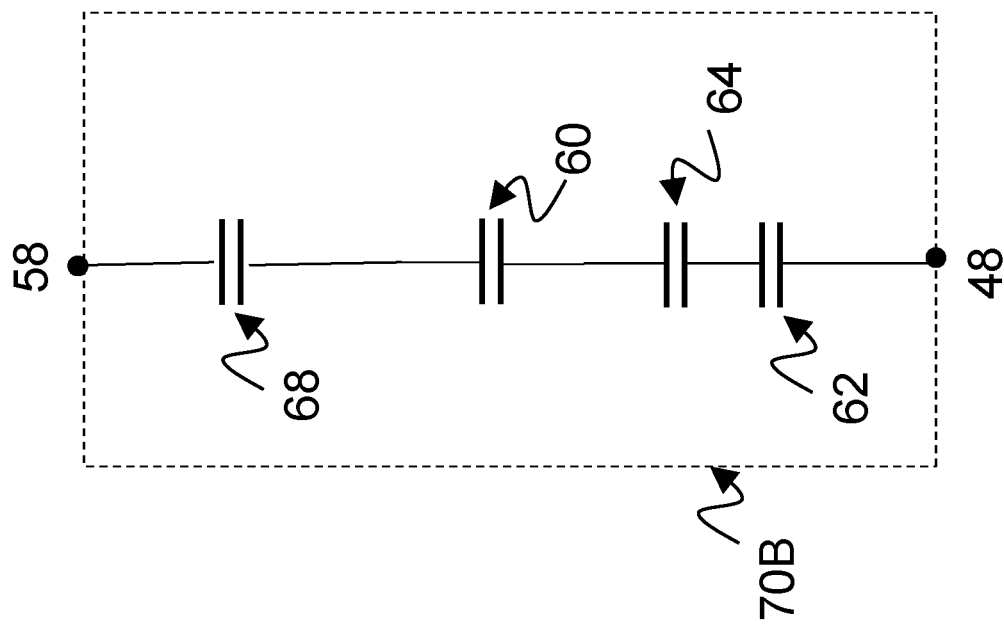
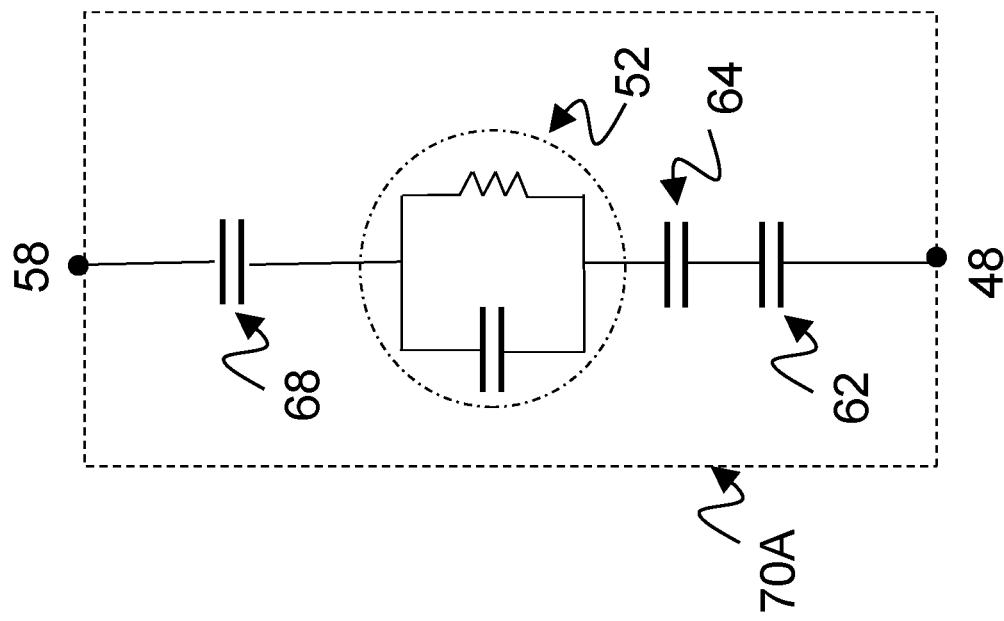

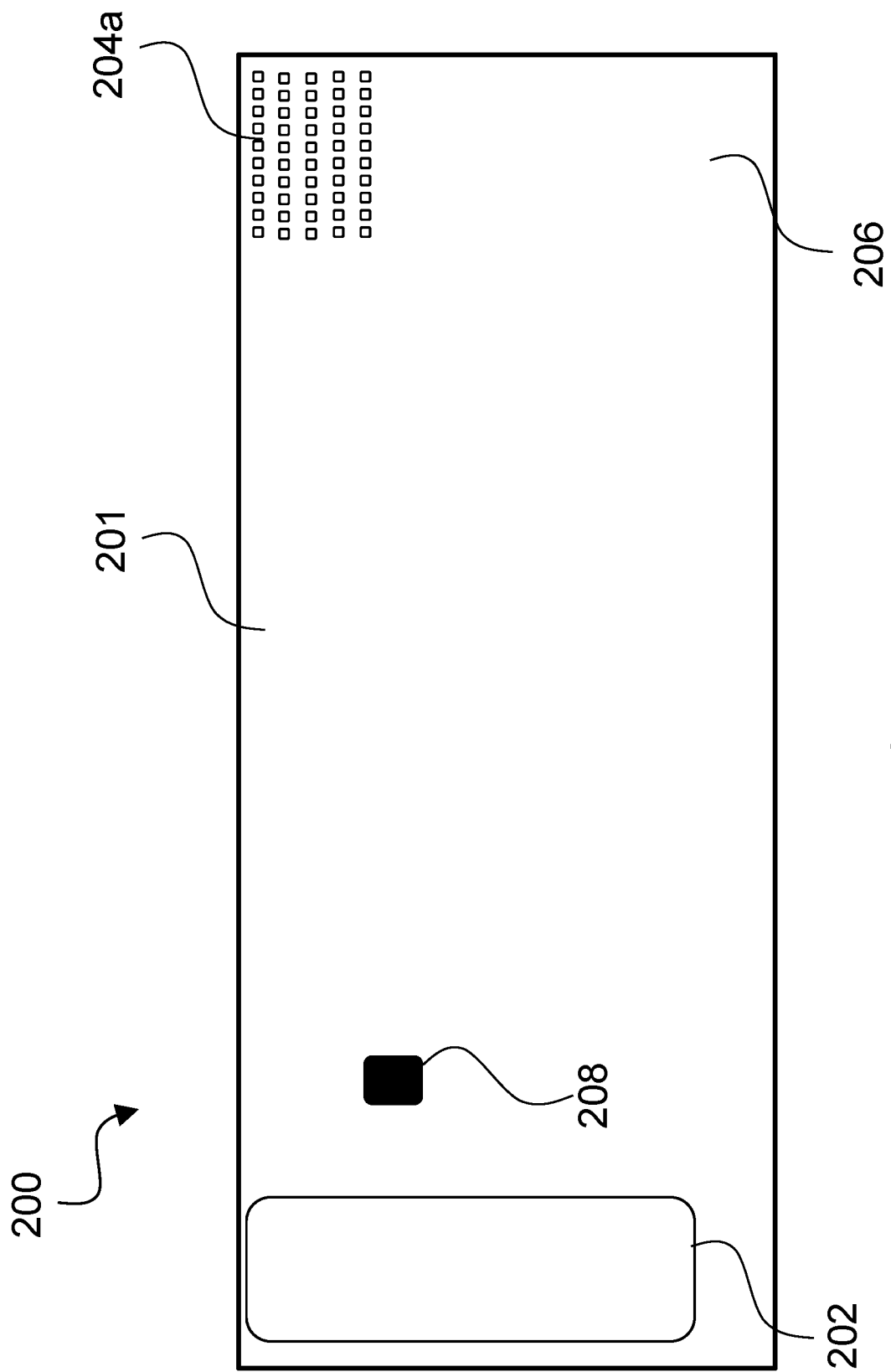

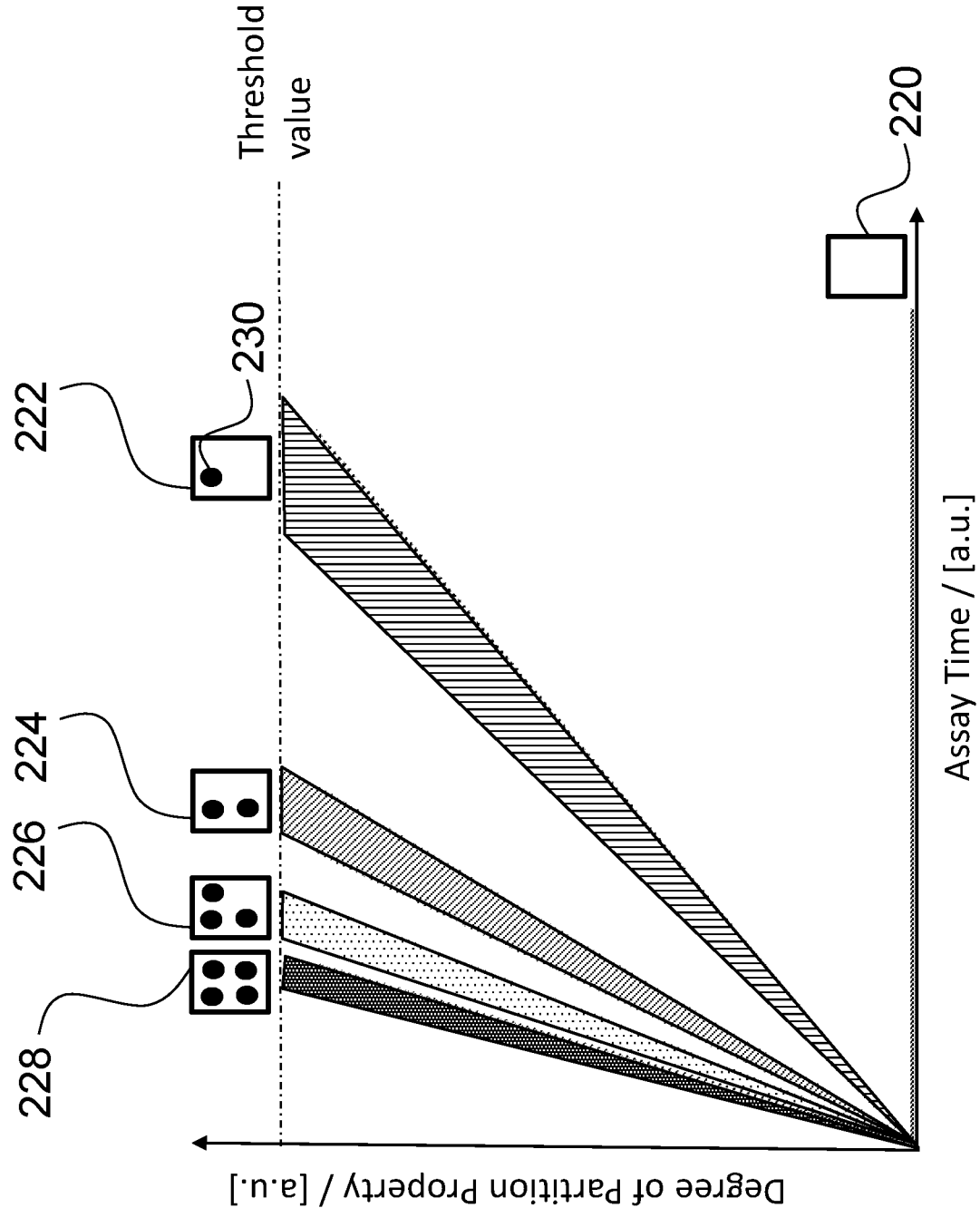

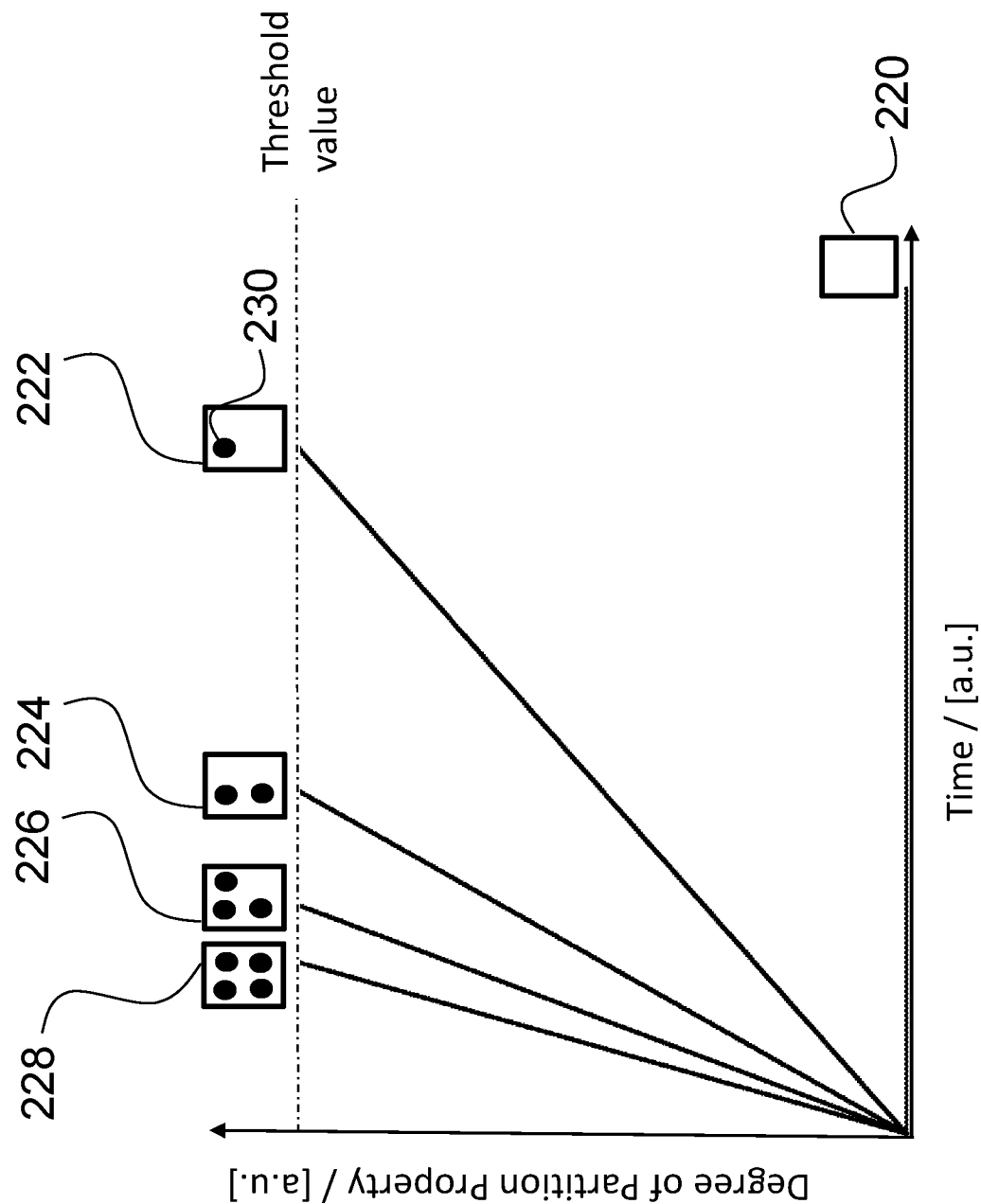

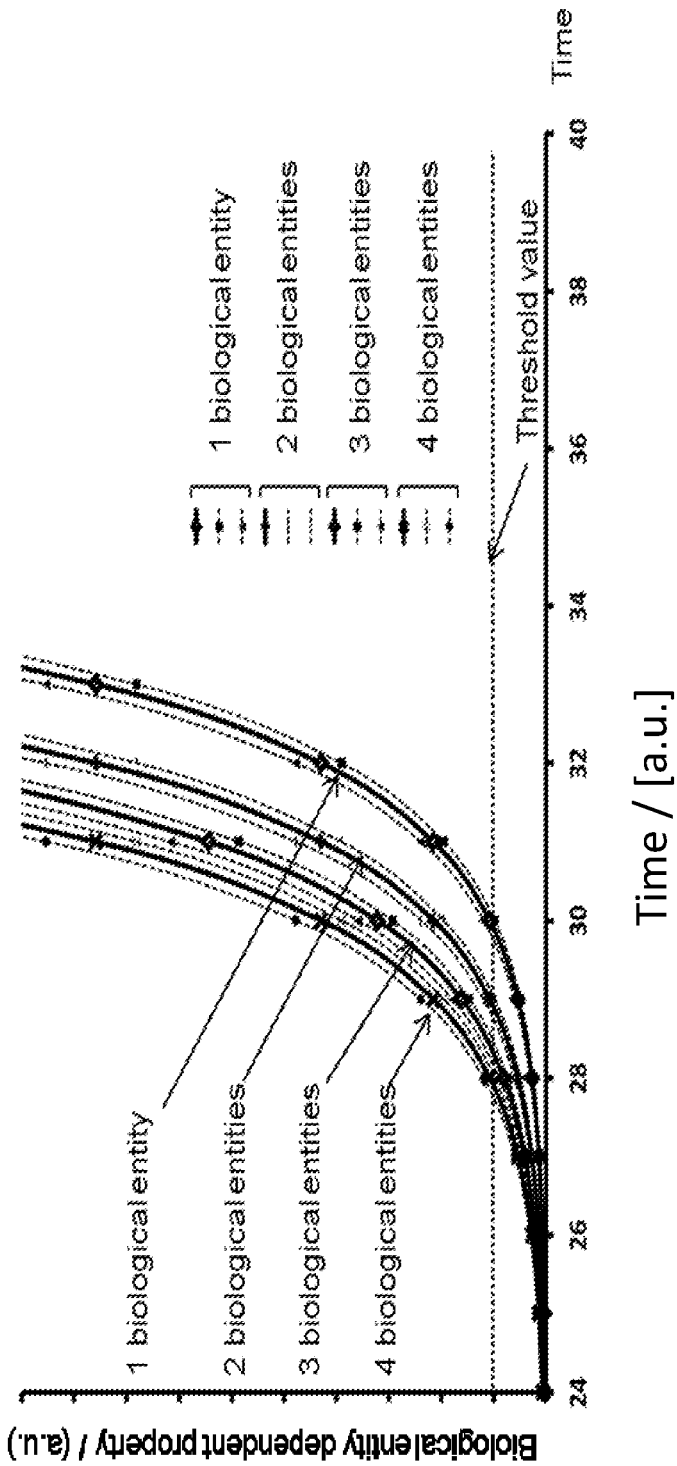

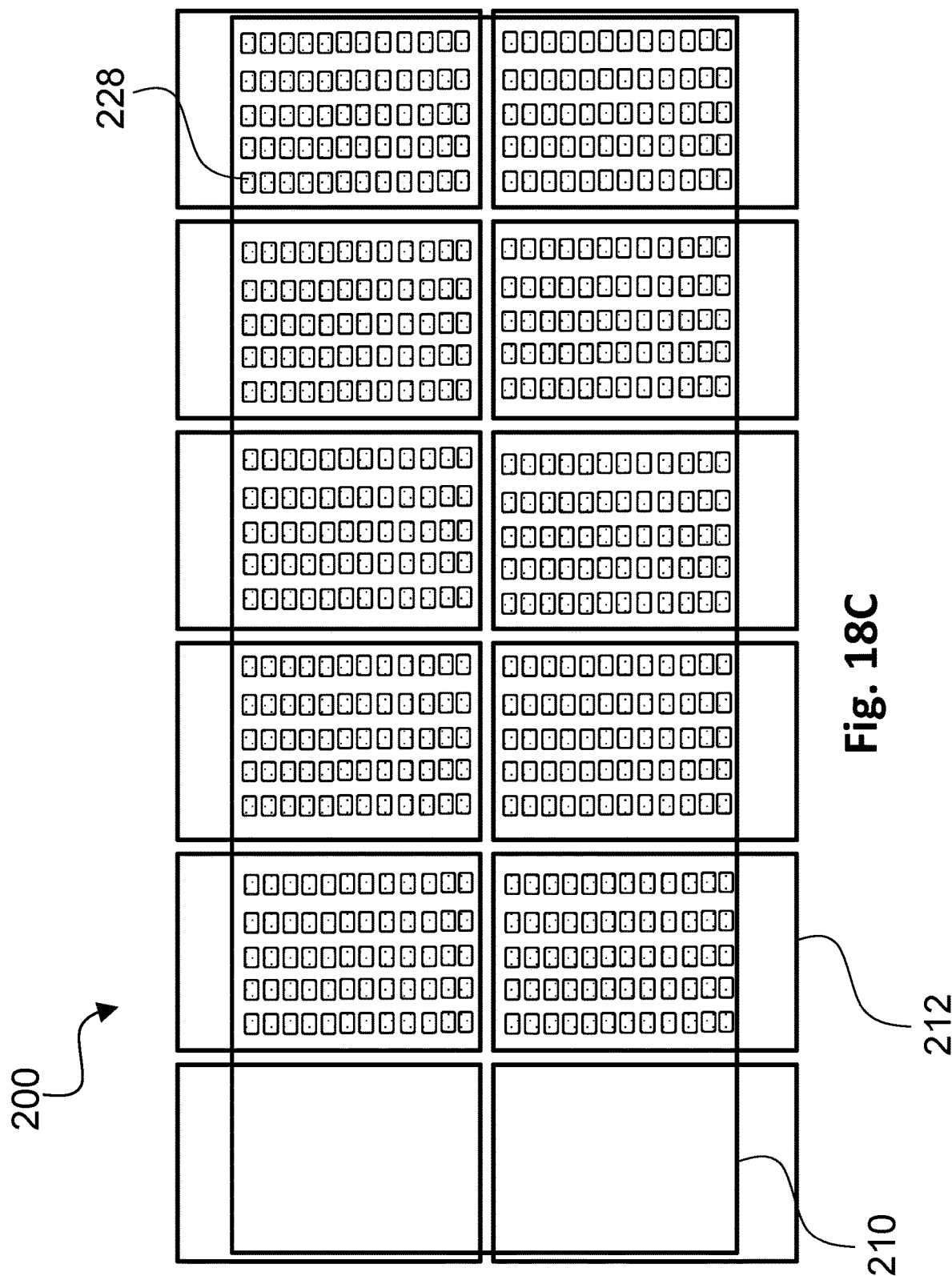

US 11,207,686 B2

MICROFLUIDIC DEVICE AND METHODS FOR DIGITAL ASSAYS IN BIOLOGICAL ANALYSES

TECHNICAL FIELD

The present invention relates generally to Active Matrix Electro-wetting-On-Dielectric (AM-EWOD) devices and to digital assays in biological analyses, such as for example digital polymerase chain reaction (PCR) for nucleic acid quantitation, enzyme-linked immunosorbent assays (ELISA) for protein biomarker quantitation, enzymatic assays for quantitation of enzymatic turnover, and cell-based assays for phenotyping and genotyping. More particularly, the present invention relates to systems and methods of performing digital assays in biological analyses on an AM-EWOD device.

BACKGROUND ART

Electrowetting on dielectric (EWOD) is a well-known technique for manipulating droplets of fluid by the application of an electric field. Active Matrix EWOD (AM-EWOD) refers to implementation of EWOD in an active matrix array incorporating transistors, for example by using thin film transistors (TFTs). It is thus a candidate technology for digital microfluidics for lab-on-a-chip technology. An introduction to the basic principles of the technology can be found in "Digital microfluidics: is a true lab-on-a-chip possible?", R. B. Fair, Microfluid Nanofluid (2007) 3:245-281).

FIG. 1 shows a part of a conventional EWOD device in cross section. The device includes a lower substrate 10, the uppermost layer of which is formed from a conductive material which is patterned so that a plurality of array element electrodes 12 (e.g., 12A and 12B in FIG. 1) are realized. The electrode of a given array element may be termed the element electrode 12. A liquid droplet 14, including a polar material (which is commonly also aqueous and/or ionic), is constrained in a plane between the lower substrate 10 and a top substrate 16. A suitable gap between the two substrates may be realized by means of a spacer 18, and a non-polar surround fluid 20 (e.g. oil) may be used to occupy the volume not occupied by the liquid droplet 14. An insulator layer 22 disposed upon the lower substrate 10 separates the conductive element electrodes 12A, 12B from a first hydrophobic coating 24 upon which the liquid droplet 14 sits with a contact angle 26 represented by θ. The hydrophobic coating is formed from a hydrophobic material (commonly, but not necessarily, a fluoropolymer).

On the top substrate 16 is a second hydrophobic coating 28 with which the liquid droplet 14 may come into contact. Interposed between the top substrate 16 and the second hydrophobic coating 28 is a reference electrode 30.

The contact angle θ is defined as shown in FIG. 1, and is determined by the balancing of the surface tension components between the solid-to liquid ($\gamma_{SL}$), the liquid-to non-polar surrounding fluid ($\gamma_{LG}$) and the solid to non-polar surrounding fluid ($\gamma_{SG}$) interfaces, and in the case where no voltages are applied satisfies Young's law, the equation being given by:

$$\cos\theta = \frac{\gamma_{SG} - \gamma_{SL}}{\gamma_{LG}} \quad \text{(equation 1)}$$

In operation, voltages termed the EW drive voltages, (e.g. $V_T$, $V_0$ and $V_{00}$ in FIG. 1) may be externally applied to different electrodes (e.g. reference electrode 30, element electrodes 12, 12A and 12B, respectively). The resulting electrical forces that are set up effectively control the hydrophobicity of the hydrophobic coating 24. By arranging for different EW drive voltages (e.g. $V_0$ and $V_{00}$) to be applied to different element electrodes (e.g. 12A and 12B), the liquid droplet 14 may be moved in the lateral plane between the two substrates 10 and 16.

Example configurations and operation of EWOD devices are described in the following. U.S. Pat. No. 6,911,132 (Pamula et al., issued Jun. 28, 2005) discloses a two-dimensional EWOD array to control the position and movement of droplets in two dimensions. U.S. Pat. No. 6,565,727 (Shenderov, issued May 20, 2003) further discloses methods for other droplet operations including the splitting and merging of droplets, and the mixing together of droplets of different materials. U.S. Pat. No. 7,163,612 (Sterling et al., issued Jan. 16, 2007) describes how TFT based thin film electronics may be used to control the addressing of voltage pulses to an EWOD array by using circuit arrangements very similar to those employed in AM display technologies.

The approach of U.S. Pat. No. 7,163,612 may be termed "Active Matrix Electrowetting on Dielectric" (AM-EWOD). There are several advantages in using TFT based thin film electronics to control an EWOD array, namely:

- Electronic driver circuits can be integrated onto the lower substrate 10.
- TFT-based thin film electronics are well suited to the AM-EWOD application. They are cheap to produce so that relatively large substrate areas can be produced at relatively low cost.
- TFTs fabricated in standard processes can be designed to operate at much higher voltages than transistors fabricated in standard CMOS processes. This is significant since many EWOD technologies require electro-wetting voltages in excess of 20V to be applied.

EWOD droplet manipulation devices are a highly desirable platform for automation of chemical and biochemical reactions. Such devices may carry out chemical/biochemical reactions or reaction sequences in droplets that require complex droplet operations that might include complex temperature profiles. Different steps of the reactions may need to be performed at different temperatures. There are many applications of EWOD devices that require the temperature of the sample and reagent droplets (and the products produced by combining them together) to be varied to facilitate the desired chemical or biochemical reaction. Many of these reaction protocols require droplets to be taken to multiple different temperatures at different times in the reaction sequence. Many reaction protocols require the droplets to be thermally cycled in time, in some cases undergoing many such thermal cycles.

A biological assay generally is defined as an assay that quantifies the concentration or activity of a biological entity in a sample container. An assay readout may be performed, for example, using absorption spectroscopy, fluorescence spectroscopy or non-optical chemical-based methods of detection of a biological entity. In digital biological assays, biological entities are partitioned into many small containers or partitions, and these partitions may be droplets in an emulsion or chambers that are physically isolated. The number of biological entities in each container is a discrete number (e.g., 0, 1, 2, 3, 4 . . . ). In addition, all partitions contain the reagents necessary for a biochemical/chemical reaction that is initiated by the biological entity. These reagents are present at a much higher concentration than the biological entity and are therefore present in all partitions at essentially the same concentration.

After partitioning, the environment of the partitions is changed, and the biological entity initiates a transformation of the reagents present in the partition into a new product substance in response to the environmental change. The presence of the new substance in the partition causes a change in a property of the partition, such as for example a change in fluorescence, absorption, electrochemical behaviour, pH, or some other physical property that can then be related to the transformation. For example, the partition property may be indicative of a concentration of the new product substance that results from the biological activity that occurs in response to the change of environment. The measurement of the partition property in turn may be used to ascertain the number of biological entities (which may be zero) respectively in each partition.

The following are common examples of digital biological assays. Digital nucleic acid assays are performed to quantify the concentration of a nucleic acid sequence. For example, a sample containing target DNA, polymerase chain reaction (PCR) reagents and fluorescent probes (alternatively readout is carried out by some other property of the droplet such as absorption, electrochemical characteristics, pH and others) may be partitioned. A commercial digital PCR system typically will generate between 1000 and 10 million partitions. The partitions are then thermal cycled at least 30 times as is known in the art for PCR assays. DNA in DNA-containing partitions is amplified, and a DNA containing partition will become fluorescent. No DNA amplification occurs in the DNA-free partitions and these droplets do not become fluorescent. After thermal cycling, the partitions are assessed individually to determine whether or not there has been a change in the partition property. The proportion of non-fluorescent partitions is analysed with Poisson statistics to calculate the original number of target DNA molecules. Knowing the original sample volume before partitioning allows the concentration of the original DNA target to be calculated.

Digital protein assays may be used to quantify proteins in samples, particularly low abundance biomarker proteins in serum samples using enzyme-linked immunosorbent assays (ELISA). ELISA is a widely used technique to detect any protein that can be bound to an antibody, or to quantify enzymes that have enzymatic activity. An enzyme sample may be partitioned into partitions containing enzyme and partitions free from enzyme. The enzyme acts on a substrate and the modified substrate generates a change in partition properties. Partitions in which this change has occurred are counted as containing enzyme, and those partitions in which the change has not occurred are counted as being enzyme free. The number of enzyme free partitions allows the original number of enzymes to be estimated. Alternatively, the spread in activity levels of individual enzymes in a population may be assessed by comparing the relative rates of formation of enzyme modified substrate.

Digital cell-based assays involve the encapsulation of discrete numbers of cells in partitions and the measuring of features of cell phenotype and genotype using, for example, cell secretions, cell surface biomarkers, cell metabolites and the like. Such assays are performed usually by partitioning cells into partitions containing fluorogenic substrates for enzymatically amplified detection.

EWOD systems have been employed to perform methods for droplet generation to form partitions, and for manipulation for digital PCR, as described for example in U.S. Pat. No. 8,137,917 (Pollack et al., issued Mar. 20, 2012). In addition, US 2016/0310949 (Kwang, published Oct. 27, 2016) describes EWOD as a method to generate and manipulate droplets for digital PCR by which standard end-point analysis is refined by including data from droplet melting experiments. These patent documents describe end-point analysis of PCR reactions and do not assess real time data. Fluidigm product qdPCR 37K IFC is a chip for compartmentalizing sub-nanolitre volumes (0.85 nl) and is used for real-time digital PCR. The system combines end-point analysis of digital PCR with simultaneous real-time fluorescence measurements enabling threshold values to be calculated for each compartment. Thermofisher QuantStudio 3D is another system for compartmentalizing biological samples for digital nucleic analysis.

It is also known that variations in partition size can have an impact on the accuracy of digital biological assays, and in particular digital PCR (Scientific Reports DOI:10.1038/srep13174). Data analysis methods, therefore, have been developed in an attempt to take this variation into account (Scientific Reports DOI:10.1038/s41598-017-09183-4).

As described above, conventional digital biological assays may be used to count the number of biological entities in a sample, such as for example DNA, RNA, and proteins, or to assess enzyme activity of individual enzymes in an enzyme sample, or to measure the features of cells in a population of cells. The conventional systems and methods, however, suffer from inaccuracies in output from digital biological assays because they do not have a convenient way to influence the distribution of partition sizes, to characterize variations in partition size (both as a consequence of partitioning and due to unexpected changes in partition size during a digital biological assay), and incorporate such variations into the analysis. Current methods typically assume that the partitions all have identical volumes, which is not the case.

Deviations of a partition volume from the expected volume may occur for a number of reasons. For example, in water in oil emulsion systems, during partitioning slight variations in partitioning parameters may result in unpredictable differences in partition sizes. Unexpected merging of partitions (droplets) may occur, or water loss may occur from aqueous partitions, during the assay. As another example, in a compartmentalizing system, compartment size may vary within a chip and between chips in an unpredictable and difficult to measure manner, or compartments may be only partially filled.

When the partition size variations are not well characterized, it is more challenging to accurately estimate the original number of biological entities in a sample using Poisson statistics, or to assess the relative characteristics of a biological entity's activity. This is a problem for many types of digital biological assays, including for example digital PCR systems used for nucleic acid analysis, systems to assess protein concentrations, systems used to analyze enzyme activity, and for systems used to profile cell populations.

SUMMARY OF INVENTION

The present invention provides systems and methods for increasing the accuracy of digital biological assays and the ease with which digital biological assays may be performed. In exemplary embodiments, a microfluidic system includes an AM-EWOD device with an array of elements that are configured to receive one or more liquid droplets that constitute partitions for performing a digital biological assay. The microfluidic system further includes an AM-EWOD controller configured to control actuation voltages applied to the array of elements, an integrated impedance sensor integrated into the AM-EWOD device configured to measure the size of the liquid droplet partitions, and a property detection system configured to detect a partition property (e.g., optical droplet property, electrochemical droplet property, pH). The controller further is configured, based on the partition property detected by the detection system, to determine a change in a biological entity initiated partition property of the liquid droplet partitions. The microfluidic system further may include at least one thermal control element and a thermal controller configured to control the temperature in the liquid droplet partitions, and a computer-based control system to store the history of each partition.

The AM-EWOD controller operates to control the environment of the partitions closely to minimize variations in the physical properties of the partitions. The following are exemplary partition properties that may be controlled: temperature of partitions, height of partitions (i.e. distance between the top and bottom of the device), and surfaces with which the partitions are in contact. This enhanced control means that measured partition properties, such as optical fluorescence measurements or other property measurements, are made in essentially a fixed volume of the partitions with minimal variations. By rendering volume variations among the partitions negligible, the determined results for the partitions are accurate and easily compared from partition to partition.

The present disclosure describes AM-EWOD based microfluidic systems and methods that automate: the partitioning of a sample into a plurality of partitions in an iterative process such that deficiencies in partitioning accuracy of the system are minimized, and the result is a population of partitions within a defined mean partition volume and standard deviation; the triggering of the start of a biological entity initiated process that causes the properties of the partitions to be modified; the measurement of the partition volumes with respect to time in real time during the assay; the measurement of the biological entity initiated new product substance with respect to time; the calculation of the relative concentrations of the new product substance in each partition; the categorization of the partitions by the number of biological entities they contain after partitioning; and the calculation of the concentration of the original sample of biological entities, or a comparison of the relative activities of biological entities, dependent on the type of digital biological assay being performed.

Real-time analysis of each partition results in a time course showing the change in the partition property over time. The relative rates of formation of new product substance may be used to compare the relative activities of individual enzymes in an enzyme sample, or assess cell heterogeneity in a sample of cells. In other digital biological assays in which the primary output from the assay is the concentration of the original sample, partitions are categorized as negative partitions, which are partitions in which a change in the partition property has not occurred, or positive partitions, which are partitions in which a change in the partition property has occurred. The ratio of positive partitions to negative partitions may then be analyzed using Poisson statistics to estimate the average number of biological entities per partition. This is then converted to a concentration in the original sample by dividing by the total volume of the sample.

An aspect of the invention, therefore, is an enhanced electrowetting on dielectric (EWOD) device and a related method of performing a digital biological assay in an EWOD device. In exemplary embodiments, the method may include the steps of: inputting a sample reservoir containing biological entities and assay reagents into the EWOD device; partitioning the sample reservoir into partitions for the digital biological assay by performing electrowetting operations with the EWOD device; measuring a volume of each partition; changing a condition of the partitions to initiate the biological assay, wherein the changed condition results in the biological entities performing a biological process to generate a product substance; and performing the biological assay by the steps of: measuring a partition property and a volume of each partition in real time, wherein the partition property is indicative of the product substance generated by the biological process of any biological entity or entities within a respective partition; determining a concentration of the product substance in each partition based on the measured partition property and volume; and categorizing the partitions by a number of biological entities contained in each partition based on the determined concentration of the product substance. Based on such categorization, the number of biological entities may be calculated, which in turn may be used to calculate the total number of biological entities or concentration in the sample reservoir.

Exemplary embodiments of the method further include an enhanced partitioning process that minimizes variation in the volume of the partitions. The enhanced partitioning process includes performing at least one iteration of a partitioning process until a sufficient portion of the sample reservoir is partitioned, wherein each iteration comprises: performing an electrowetting operation to pull a plurality of sample droplets from the sample reservoir; measuring a volume of each sample droplet with a sensing system on the EWOD device; calculating a mean droplet volume and setting an acceptable range of variation of droplet volume relative to the mean droplet volume; performing an electrowetting operation to isolate partitions within the acceptable range in an assay area of the EWOD device; and performing an electrowetting operation to merge partitions outside of the acceptable range back into the sample reservoir. In exemplary embodiments, multiple iterations of the portioning process are performed.

According to another aspect of the invention, a microfluidic system includes an electro-wetting on dielectric (EWOD) device comprising an element array configured to receive one or more liquid droplets, the element array comprising a plurality of individual array elements; and a control system configured to control actuation voltages applied to the element array to perform manipulation operations to the liquid droplets to perform the method of performing a digital biological assay according to any of the embodiments. A plurality of thermal control elements may be located at different spatial locations along the EWOD device, and wherein the control system includes a thermal control unit configured to control temperatures of the plurality of thermal control elements to generate a plurality of thermal zones located at different spatial locations along the EWOD device. The microfluidic system further may include a light source that emits light onto the array elements, and an optical sensor configured to sense an optical property of liquid droplets dispensed onto the array elements. The microfluidic system further may include integrated impedance sensing circuitry that is integrated into the array elements of the EWOD device, and a volume of liquid droplets dispensed onto the array elements is determined based on an impedance sensed by the impedance sensing circuitry.

Another aspect of the invention is a non-transitory computer-readable medium storing program code which is executed by a processing device for controlling actuation voltages applied to array elements of an element array of an electro-wetting on dielectric (EWOD) device for performing droplet manipulations on droplets on the element array, the program code being executable by the processing device to perform the steps of the method of performing a digital biological assay in an EWOD device accordingly to any of the embodiments.

These and further features of the present invention will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the spirit and terms of the claims appended hereto. Features that are described and/or illustrated with respect to one embodiment may be used in the same way or in a similar way in one or more other embodiments and/or in combination with or instead of the features of the other embodiments.

BRIEF DESCRIPTION OF DRAWINGS

FIG. 4 is a drawing depicting a cross section through some of the array elements of the exemplary AM-EWOD device of FIG. 3.

FIG. 5A is a drawing depicting a circuit representation of the electrical load presented at the element electrode when a liquid droplet is present.

FIG. 5B is a drawing depicting a circuit representation of the electrical load presented at the element electrode when no liquid droplet is present.

FIGS. 12A, 12B, 12C, 12D, 12E, 12F, and 12G are drawings depicting a progression of steps constituting an exemplary method of performing a partitioning process to generate partitions for use in a biological assay reaction protocol, in accordance with embodiments of the present invention.

FIGS. 14A, 14B, and 14C are graphs depicting the degree of the partition property plotted as a function of time of a biological assay for different ranges of partition volume variation.

FIGS. 15A and 15B are graphs depicting the degree of the partition property plotted as a function of time of a biological assay for different ranges of partition volume variation, for a partition property that varies exponentially with time.

FIGS. 18A, 18B, and 18C are drawings depicting a progression of steps constituting another exemplary method of performing a partitioning process to generate partitions for use in a biological assay reaction protocol, in accordance with another embodiment of the present invention.

DESCRIPTION OF EMBODIMENTS

Figure 2:
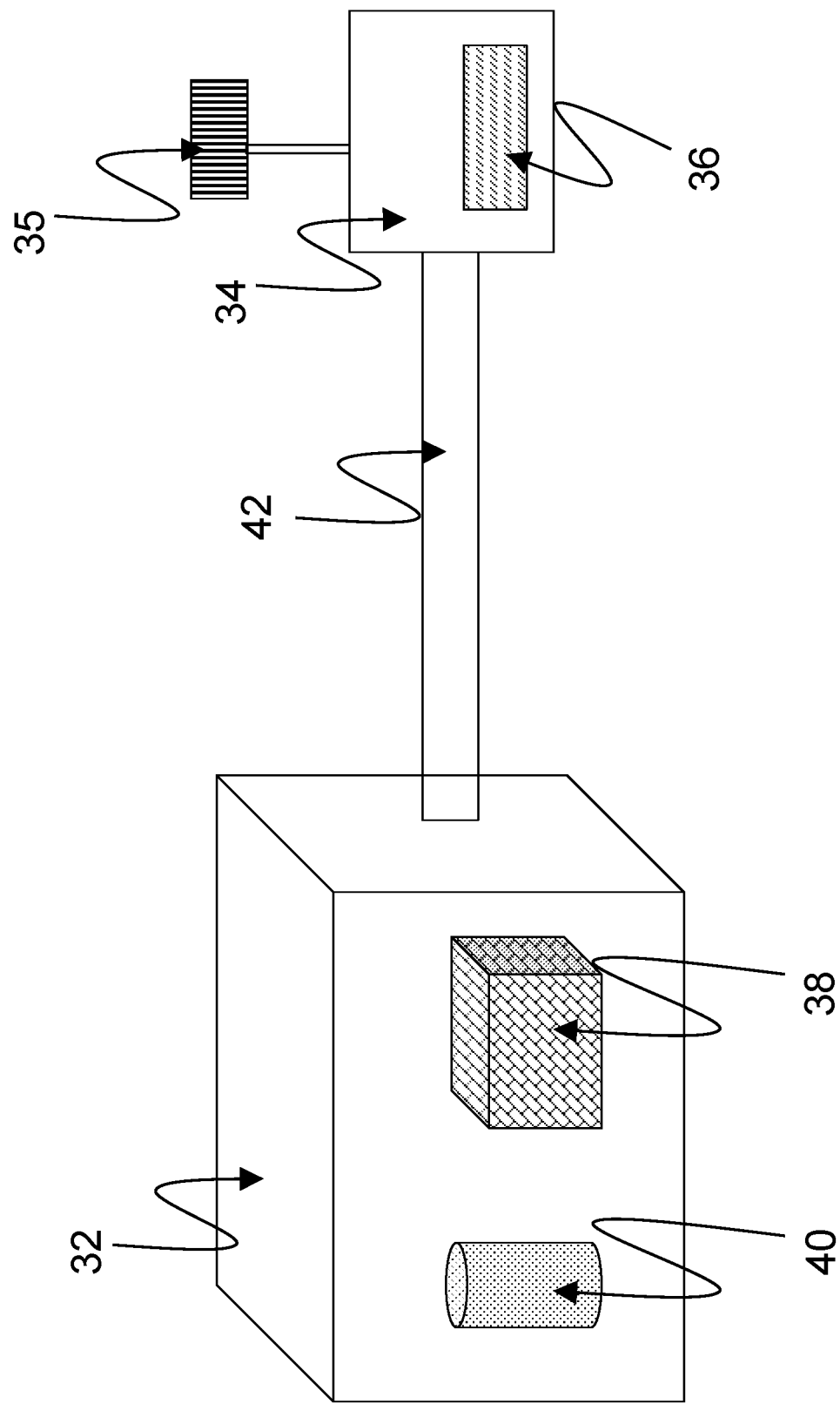
FIG. 2 is a drawing depicting an exemplary EWOD based microfluidic system according to embodiments of the present invention.

FIG. 2 is a drawing depicting an exemplary EWOD based microfluidic system according to embodiments of the present invention. In the example of FIG. 2, the measurement system includes a reader 32 and a cartridge 34. The cartridge 34 may contain a microfluidic device, such as an EWOD or AM-EWOD device 36, as well as (not shown) fluid input ports into the device and an electrical connection as are conventional. The fluid input ports may perform the function of inputting fluid into the AM-EWOD device 36 and generating droplets within the device, for example by dispensing from input reservoirs as controlled by electro-wetting. As further detailed below, the microfluidic device includes an electrode array configured to receive the inputted fluid droplets.

The microfluidic system further may include a control system configured to control actuation voltages applied to the electrode array of the microfluidic device to perform manipulation operations to the fluid droplets. For example, the reader 32 may contain such a control system configured as control electronics 38 and a storage device 40 that may store any application software any data associated with the system. The control electronics 38 may include suitable circuitry and/or processing devices that are configured to carry out various control operations relating to control of the AM-EWOD device 36, such as a CPU, microcontroller or microprocessor.

Among their functions, to implement the features of the present invention, the control electronics may comprise a part of the overall control system that may execute program code embodied as a control application within the storage device 40. It will be apparent to a person having ordinary skill in the art of computer programming, and specifically in application programming for electronic control devices, how to program the control system to operate and carry out logical functions associated with the stored control application. Accordingly, details as to specific programming code have been left out for the sake of brevity. The storage device 40 may be configured as a non-transitory computer readable medium, such as random access memory (RAM), a read-only memory (ROM), an erasable programmable read-only memory (EPROM or Flash memory), or any other suitable medium. Also, while the code may be executed by control electronics 38 in accordance with an exemplary embodiment, such control system functionality could also be carried out via dedicated hardware, firmware, software, or combinations thereof, without departing from the scope of the invention.

The control system may be configured to perform some or all of the following functions:

Define the appropriate timing signals to manipulate liquid droplets on the AM-EWOD device 36.

Interpret input data representative of sensor information measured by a sensor or sensor circuitry associated with the AM-EWOD device 36, including computing the locations, sizes, centroids and perimeters of liquid droplets on the AM-EWOD device 36.

Use calculated sensor data to define the appropriate timing signals to manipulate liquid droplets on the AM-EWOD device 36, i.e. acting in a feedback mode.

Provide for implementation of a graphical user interface (GUI) whereby the user may program commands such as droplet operations (e.g. move a droplet), assay operations (e.g. perform an assay), and the GUI may report the results of such operations to the user.

In accordance with embodiments of the present invention, and as further detailed below, the control system may include a thermal control unit configured to control temperature of the EWOD device within the EWOD channel as is suitable for a given reaction protocol.

In the example of FIG. 2, an external sensor module 35 may be provided for sensing droplet properties. For example, optical sensors as are known in the art may be employed as external sensors for sensing droplet properties. Suitable optical sensors include camera devices, light sensors, charged coupled devices (CCDs) and image similar image sensors, and the like. A sensor alternatively may be configured as internal sensor circuitry incorporated as part of the drive circuitry in each array element. Such sensor circuitry may sense droplet properties by the detection of an electrical property at the array element, such as impedance or capacitance.

The control system, such as via the control electronics 38, may supply and control the actuation voltages applied to the electrode array of the microfluidics device 36, such as required voltage and timing signals to perform droplet manipulation operations and sense liquid droplets on the AM-EWOD device 36. The control electronics further may execute the application software to generate and output control voltages for droplet sensing and performing sensing operations. The reader 32 and cartridge 34 may be electrically connected together while in use, for example by a cable of connecting wires 42, although various other methods (e.g. wireless connection) of providing electrical communication may be used as are known to those of ordinary skill in the art.

Figure 3:
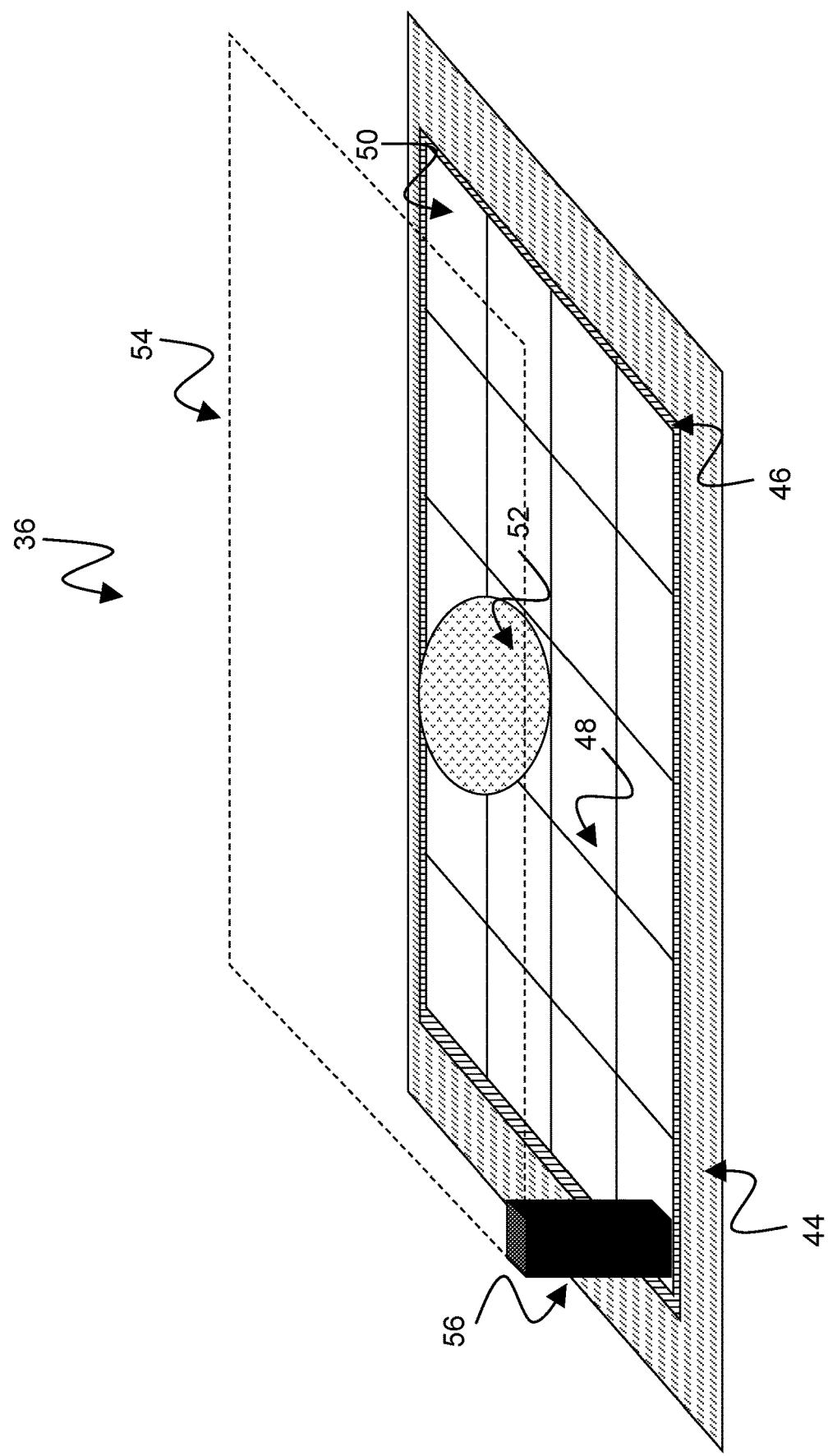
FIG. 3 is a drawing depicting an exemplary AM-EWOD device in schematic perspective in accordance with embodiments of the present invention.

FIG. 3 is a drawing depicting additional details of the exemplary AM-EWOD device 36 in schematic perspective in accordance with embodiments of the present invention.

The AM-EWOD device 36 has a lower substrate 44 with thin film electronics 46 disposed upon the lower substrate 44. The thin film electronics 46 are arranged to drive array element electrodes 48. A plurality of array element electrodes 48 are arranged in an electrode or element array 50, having X by Y array elements where X and Y may be any integer. A liquid droplet 52 which may include any polar liquid and which typically may be aqueous, is enclosed between the lower substrate 44 and a top substrate 54 separated by a spacer 56, although it will be appreciated that multiple liquid droplets 52 can be present.

FIG. 4 is a drawing depicting a cross section through some of the array elements of the exemplary AM-EWOD 36 device of FIG. 3. In the portion of the AM-EWOD device depicted in FIG. 4, the device includes a pair of the array element electrodes 48A and 48B that are shown in cross section that may be utilized in the electrode or element array 50 of the AM-EWOD device 36 of FIG. 3. The device configuration is similar to the conventional configuration shown in FIG. 1, with the AM-EWOD device 36 further incorporating the thin-film electronics 46 disposed on the lower substrate 44, which is separated from the upper substrate 54 by the spacer 56. The uppermost layer of the lower substrate 44 (which may be considered a part of the thin film electronics layer 46) is patterned so that a plurality of the array element electrodes 48 (e.g. specific examples of array element electrodes are 48A and 48B in FIG. 4) are realized. The term element electrode 48 may be taken in what follows to refer both to the physical electrode structure 48 associated with a particular array element, and also to the node of an electrical circuit directly connected to this physical structure. A reference electrode 58 is shown in FIG. 4 disposed upon the top substrate 54, but the reference electrode alternatively may be disposed upon the lower substrate 44 to realize an in-plane reference electrode geometry. The term reference electrode 58 may also be taken in what follows to refer to both or either of the physical electrode structure and also to the node of an electrical circuit directly connected to this physical structure.

Figure 1:
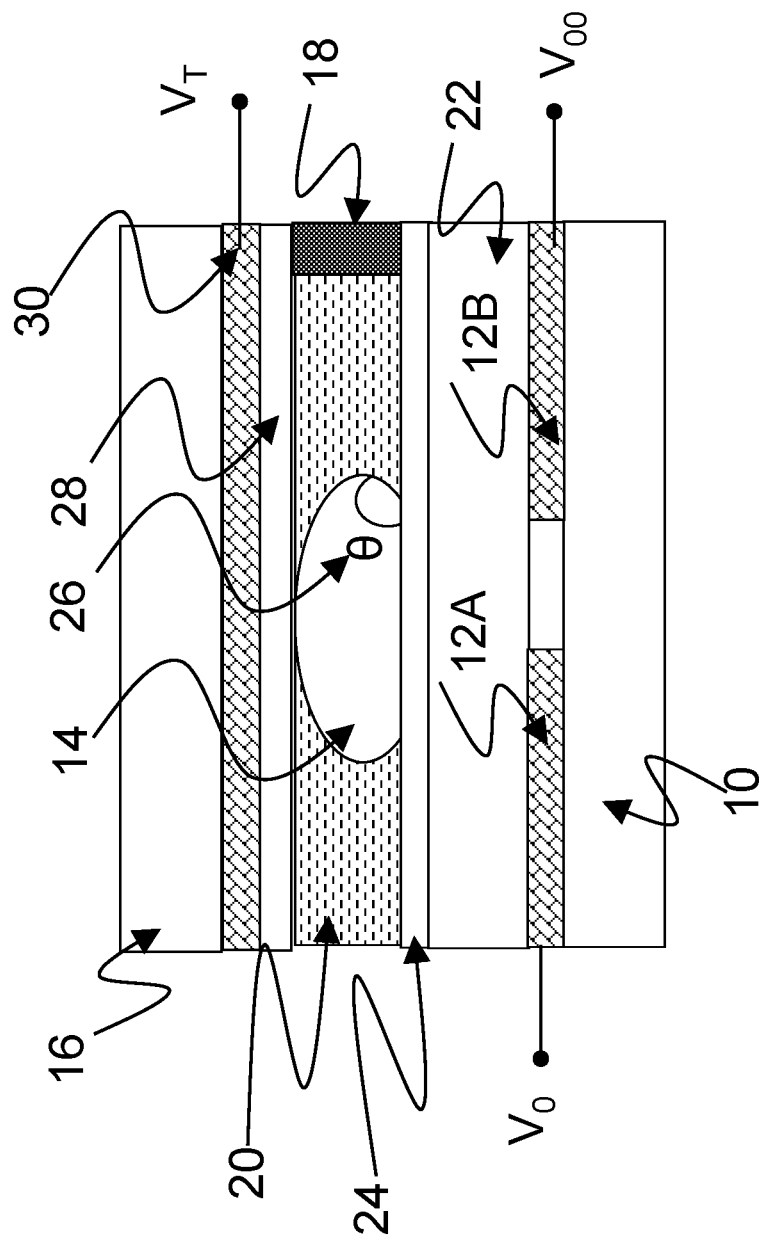
FIG. 1 is a drawing depicting a conventional EWOD device in cross-section.

Also similarly to the conventional structure of FIG. 1, in the AM-EWOD device 36, a non-polar fluid 60 (e.g. oil) may be used to occupy the volume not occupied by the liquid droplet 52. An insulator layer 62 may be disposed upon the lower substrate 44 that separates the conductive element electrodes 48A and 48B from a first hydrophobic coating 64 upon which the liquid droplet 52 sits with a contact angle 66 represented by θ. The hydrophobic coating is formed from a hydrophobic material (commonly, but not necessarily, a fluoropolymer). On the top substrate 54 is a second hydrophobic coating 68 with which the liquid droplet 52 may come into contact. The reference electrode 58 is interposed between the top substrate 54 and the second hydrophobic coating 68.

FIG. 5A shows a circuit representation of the electrical load 70A between the element electrode 48 and the reference electrode 58 in the case where a liquid droplet 52 is present. The liquid droplet 52 can usually be modeled as a resistor and capacitor in parallel. Typically, the resistance of the droplet will be relatively low (e.g. if the droplet contains ions) and the capacitance of the droplet will be relatively high (e.g. because the relative permittivity of polar liquids is relatively high, e.g. ~80 if the liquid droplet is aqueous). In many situations the droplet resistance is relatively small, such that at the frequencies of interest for electro-wetting, the liquid droplet 52 may function effectively as an electrical short circuit. The hydrophobic coatings 64 and 68 have electrical characteristics that may be modelled as capacitors, and the insulator 62 may also be modelled as a capacitor. The overall impedance between the element electrode 48 and the reference electrode 58 may be approximated by a capacitor whose value is typically dominated by the contribution of the insulator 62 and hydrophobic coatings 64 and 68 contributions, and which for typical layer thicknesses and materials may be on the order of a pico-Farad in value.

FIG. 5B shows a circuit representation of the electrical load 70B between the element electrode 48 and the reference electrode 58 in the case where no liquid droplet is present. In this case the liquid droplet components are replaced by a capacitor representing the capacitance of the non-polar fluid 60 which occupies the space between the top and lower substrates. In this case the overall impedance between the element electrode 48 and the reference electrode 58 may be approximated by a capacitor whose value is dominated by the capacitance of the non-polar fluid and which is typically small, of the order of femto-Farads.

For the purposes of driving and sensing the array elements, the electrical load 70A/70B overall functions in effect as a capacitor, whose value depends on whether a liquid droplet 52 is present or not at a given element electrode 48. In the case where a droplet is present, the capacitance is relatively high (typically of order pico-Farads), whereas if there is no liquid droplet present the capacitance is low (typically of order femto-Farads). If a droplet partially covers a given electrode 48 then the capacitance may approximately represent the extent of coverage of the element electrode 48 by the liquid droplet 52.

Figure 6:
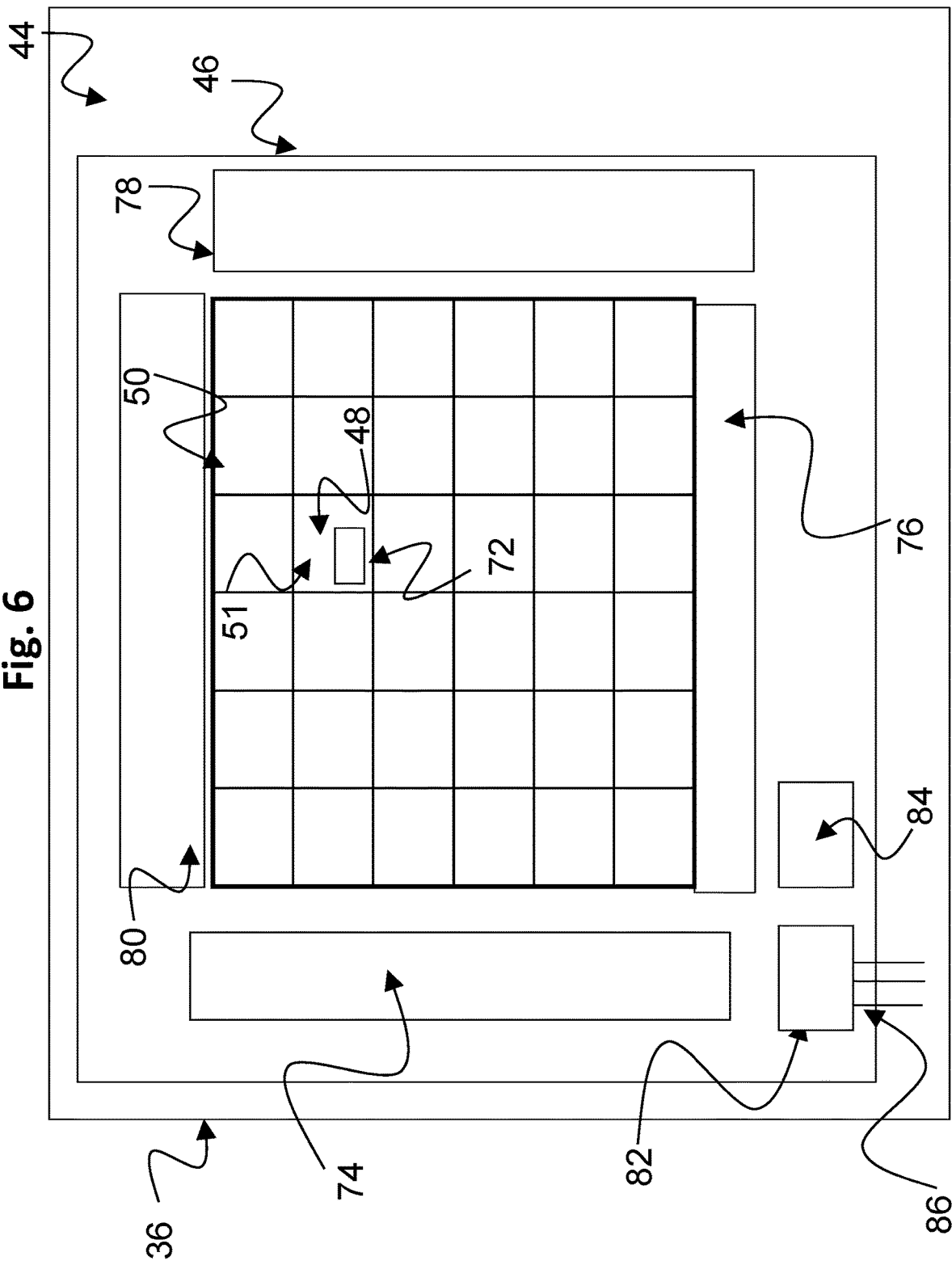
FIG. 6 is a drawing depicting an exemplary arrangement of thin film electronics in the exemplary AM-EWOD device of FIG. 3 in accordance with embodiments of the present invention.

FIG. 6 is a drawing depicting an exemplary arrangement of thin film electronics 46 in the exemplary AM-EWOD device 36 of FIG. 3 in accordance with embodiments of the present invention. The thin film electronics 46 is located upon the lower substrate 44. Each array element 51 of the array of elements 50 contains an array element circuit 72 for controlling the electrode potential of a corresponding element electrode 48. Integrated row driver 74 and column driver 76 circuits are also implemented in thin film electronics 46 to supply control signals to the array element circuit 72. The array element circuit 72 may also contain a sensing capability for detecting the presence or absence of a liquid droplet in the location of the array element. Integrated sensor row addressing 78 and column detection circuits 80 may further be implemented in thin film electronics for the addressing and readout of the sensor circuitry in each array element.

A serial interface 82 may also be provided to process a serial input data stream and facilitate the programming of the required voltages to the element electrodes 48 in the array 50. A voltage supply interface 84 provides the corresponding supply voltages, top substrate drive voltages, and other requisite voltage inputs as further described herein. A number of connecting wires 86 between the lower substrate 44 and external control electronics, power supplies and any other components can be made relatively few, even for large array sizes. Optionally, the serial data input may be partially parallelized. For example, if two data input lines are used the first may supply data for columns 1 to X/2, and the second for columns (1+X/2) to M with minor modifications to the column driver circuits 76. In this way the rate at which data can be programmed to the array is increased, which is a standard technique used in Liquid Crystal Display driving circuitry.

Generally, an exemplary AM-EWOD device 36 that includes thin film electronics 46 may be configured as follows. The AM-EWOD device 36 includes the reference electrode 58 mentioned above (which, optionally, could be an in-plane reference electrode) and a plurality of individual array elements 51 on the array of elements 50, each array element 51 including an array element electrode 48 and array element circuitry 72. Relatedly, the AM-EWOD device 36 may be configured to perform a method of actuating the array elements to manipulate liquid droplets on the array by controlling an electro-wetting voltage to be applied to a plurality of array elements. The applied voltages may be provided by operation of the control system described as to FIG. 2, including the control electronics 38 and applications and data stored on the storage device 40. The electro-wetting voltage at each array element 51 is defined by a potential difference between the array element electrode 48 and the reference electrode 58. The method of controlling the electro-wetting voltage at a given array element typically includes the steps of supplying a voltage to the array element electrode 48, and supplying a voltage to the reference electrode 58, by operation of the control system.

Figure 7:
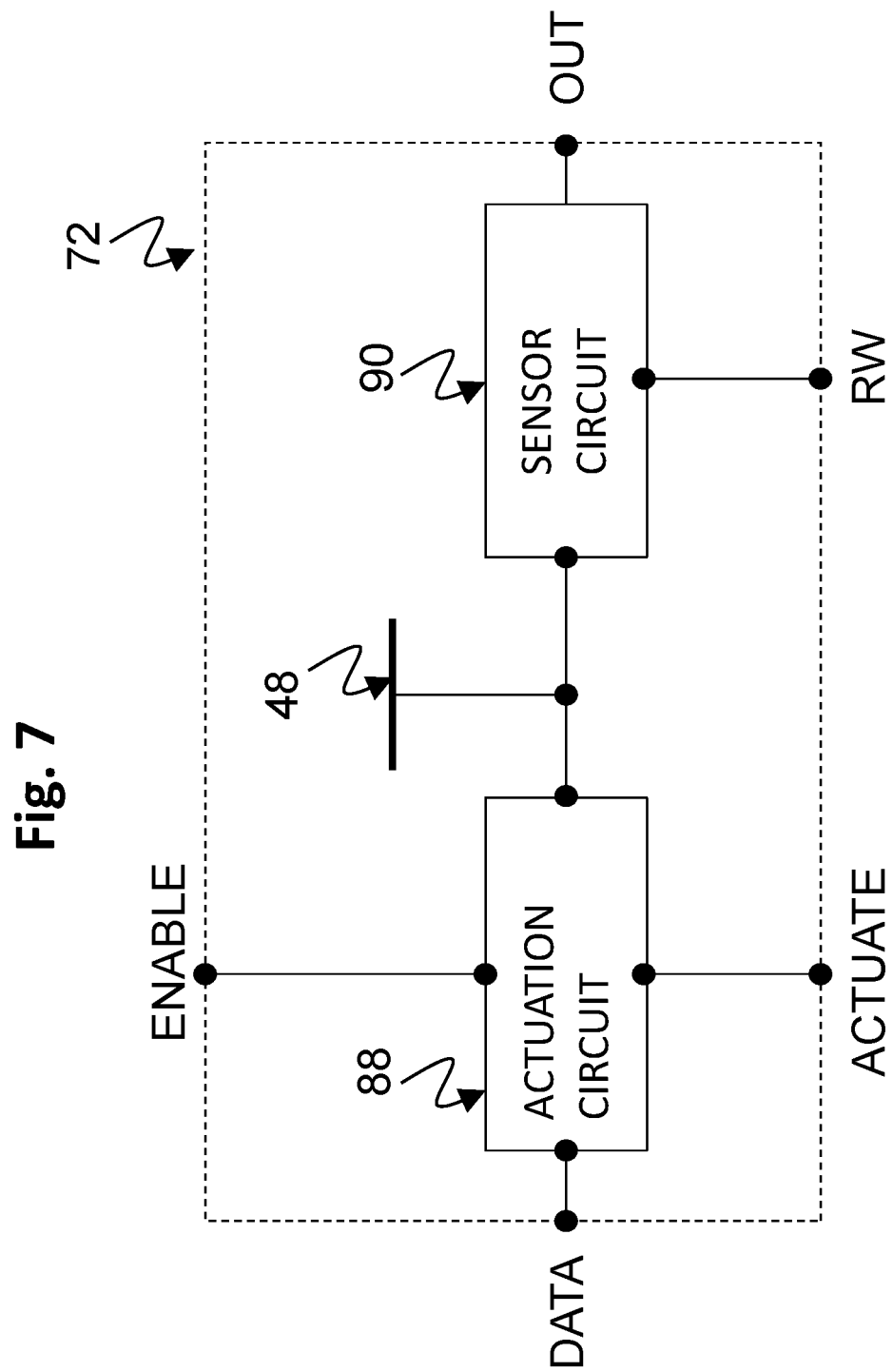
FIG. 7 is a drawing depicting an exemplary arrangement of the array element circuit in accordance with embodiments of the present invention.

FIG. 7 is a drawing depicting an exemplary arrangement of the array element circuit 72 present in each array element 51, in accordance with embodiments of the present invention. The array element circuit 72 may contain an actuation circuit 88, having inputs ENABLE, DATA and ACTUATE, and an output which is connected to an element electrode 48. The array element circuit 72 also may contain a droplet sensing circuit 90, which may be in electrical communication with the element electrode 48. Typically, the read-out of the droplet sensing circuit 90 may be controlled by one or more addressing lines (e.g. RW) that may be common to elements in the same row of the array, and may also have one or more outputs, e.g. OUT, which may be common to all elements in the same column of the array.

The array element circuit 72 may typically perform the functions of:

(i) Selectively actuating the element electrode 48 by supplying a voltage to the array element electrode. Accordingly, any liquid droplet present at the array element 51 may be actuated or de-actuated by the electro-wetting effect.

(ii) Sensing the presence or absence of a liquid droplet at the location of the array element 51. The means of sensing may be capacitive or impedance, optical, thermal or some other means. Capacitive or impedance sensing may be employed conveniently and effectively using an integrated impedance sensor circuit as part of the array element circuitry.

Exemplary configurations of array element circuits 72 including integrated impedance sensor circuitry are known in the art, and for example are described in detail in U.S. Pat. No. 8,653,832 referenced in the background art section, and commonly assigned UK application GB1500261.1, both of which are incorporated here by reference. These patent documents include descriptions of how the droplet may be actuated (by means of electro-wetting) and how the droplet may be sensed by integrated capacitive or impedance sensing circuitry. Typically, capacitive and impedance sensing may be analogue and may be performed simultaneously, or near simultaneously, at every element in the array. By processing the returned information from such a sensor (for example in the application software in the storage device 40 of the reader 32), the control system described above can determine in real-time, or almost real-time the position, size or volume, centroid and perimeter of each liquid droplet present in the array of elements 50. As referenced in connection with FIG. 2, an alternative to sensor circuitry is to provide an external sensor (e.g., sensor 35), such as an optical sensor that can be used to sense droplet properties.

Common digital biological assay methods include performing steps of the reaction protocol at different temperatures. Accordingly, the present invention uses enhanced control of temperature in an EWOD device to optimize temperature in the EWOD channel where the droplet manipulations and reactions occur. A complete description of an exemplary EWOD device incorporating enhanced temperature control is provided in Applicant's application Ser. No. 15/607,940 filed on May 30, 2017, the content of which is incorporated here by reference. For illustration purposes, a portion of such description is provided herein. It will be appreciated that the following is an example, and any suitable temperature control within the EWOD device may be employed.

Figure 8:
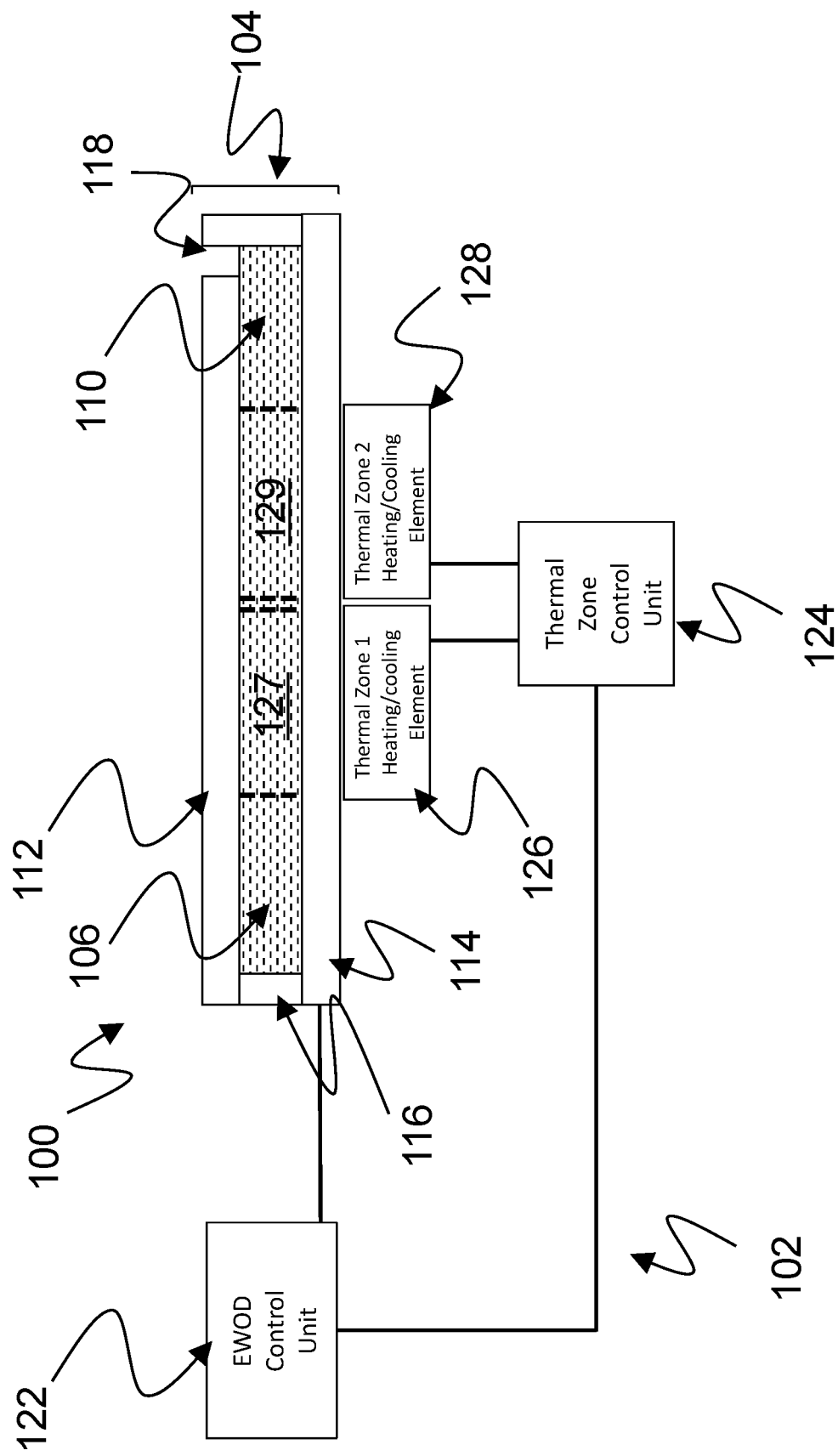
FIG. 8 is a drawing depicting an exemplary microfluidic system in accordance with embodiments of the present invention including thermal control elements.
Figure 9:
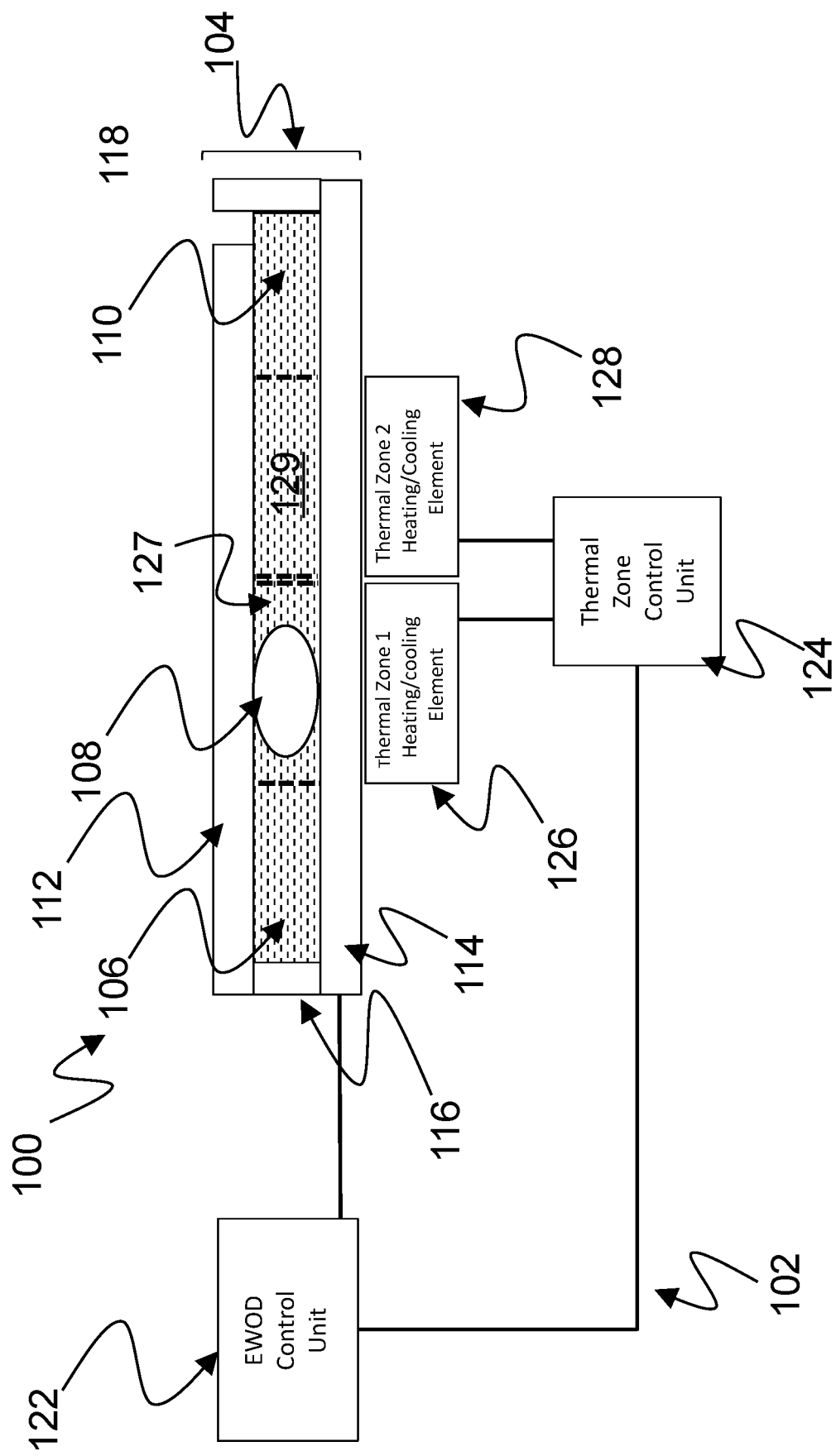
FIG. 9 is a drawing depicting the microfluidic system of FIG. 8 showing an example location of a liquid droplet within the EWOD channel.

FIG. 8 is a drawing depicting an exemplary microfluidic system 100 in accordance with embodiments of the present invention, which includes a control system 102 and an EWOD device 104 (which in particular may be an AM-EWOD device) that defines an EWOD channel 106. FIG. 9 is a drawing depicting the microfluidic system 100 of FIG. 8 showing an example location of a liquid droplet 108 within the EWOD channel 106. A non-polar fluid 110 (e.g. oil) may be used to occupy the volume not occupied by the liquid droplet 108. The EWOD device may include a first (top) substrate assembly 112 and a second (bottom) substrate assembly 114 separated by a spacer 116, which define the EWOD channel 106. For simplicity of illustration of pertinent features, the individual layers of the EWOD device components are omitted. Accordingly, the first and second substrate assemblies may include the associated substrates, insulating layers, electrode layers, and related structures that form the EWOD device, such as for example the various components described with respect to FIGS. 3-7. FIGS. 8 and 9 also show a representative fluid input structure 118 for input of fluid into the EWOD channel. Various configurations of the input structure are known in the art, and therefore any suitable input structure may be employed.

As referenced above, the microfluidic system 100 further includes a control system 102. The control system 102 may be configured comparably as the control system described in connection with FIG. 2, including control electronics that may execute program code embodied as a control application incorporated within a non-transitory computer readable medium or storage device. The control system 102 may include an EWOD control unit 122 that has control electronics and CPU processing devices for controlling the movement of droplets on the EWOD device by the control of actuation voltages applied to the array elements of the EWOD device. The control system 102 further includes a thermal zone control unit 124 and a plurality of thermal control elements. In the depicted example, two thermal control elements 126 and 128 are shown positioned at different spatial locations along the EWOD device. It will be appreciated that any suitable number of a plurality of thermal control elements may be employed in a given device as may be suitable for particular microfluidic operations. The thermal zone control unit 124, similarly as the EWOD control unit 122, contains control electronics and CPU or processing devices, for controlling the temperature of the thermal control elements to generate different temperature control zones within the EWOD device. The control electronics of the thermal zone control unit likewise may similarly execute program code embodied as a thermal control application incorporated within a non-transitory computer readable medium or storage device within the thermal zone control unit.

The thermal control elements 126 and 128 may be capable of actively heating, cooling, or both heating and cooling the EWOD device as required and as determined by the thermal zone control unit 124 in accordance with any desired reaction protocol. Heating and/or cooling may be implemented by any well-known mechanism. For example, heating may be by Joule heating or resistance heating, and cooling may be by means of the Peltier effect as are known in the art for heating and cooling. A region of the EWOD channel 106 within the EWOD device whose temperature is controlled by one of the thermal control elements is referred to herein as a thermal zone. In FIGS. 8 and 9, for example, the first thermal control element 126 is operable to control the temperature of a first thermal zone 127 within the EWOD channel, and the second thermal control element 128 is operable to control the temperature of a second thermal zone 129 within the EWOD channel. Accordingly, the first and second thermal zones 127 and 129 are located at different spatial locations along the EWOD device based on corresponding locations of the thermal control elements. Again, any suitable number of a plurality of thermal control elements may be employed, which would control temperature in a corresponding number of thermal zones located at different spatial locations along the EWOD device.

A liquid droplet assumes a temperature of any thermal zone in which the liquid droplet is located. Because of the minute size of the droplet, rapid temperature equalization occurs as between the liquid droplet and the thermal zone. In the example of FIG. 9, the liquid droplet 108 is located in the first thermal zone 127, and thus would assume the temperature of the first thermal zone 127 as controlled by the first thermal control element 126. By application of appropriate actuation voltages, the liquid droplet 108 may be moved to the second thermal zone 129, and thus would then assume the temperature of the second thermal zone 129 as controlled by the second thermal control element 128.

The EWOD control unit 122 applies actuation voltages to the array elements of the EWOD device to move liquid droplets from one thermal zone to another thermal zone. The thermal zone control unit 124 and EWOD control unit 122 are organized to work together to configure dynamically controlled thermal zones which may vary the temperature in the channel in accordance with the locations of liquid droplets within the channel of the EWOD device. The position of liquid droplets in the EWOD channel may be read out with droplet position sensors (e.g., using the external sensor 35 of FIG. 3 or the droplet sensing circuit 90 of FIG. 7 based on sensing droplet impedance) which may be integrated into the EWOD droplet manipulation device. By combining spatial and temporal control of temperature in the channel of the EWOD device, the temperature profile required for the execution of a given biochemical/chemical reaction or sequence of reactions is optimized, and in turn the number and size of the thermal zones are optimized. The inclusion of the droplet position sensor(s) further enhances the system since feedback control of the droplet position may be used to determine the time at which changes to the temperature of thermal zones are implemented.

The thermal control elements 126 and 128 may be arranged to be in thermal contact with one of the substrate layers of the EWOD device, such as being arranged on either an outer surface or internally as part of the substrate layers of the EWOD device. In the example of FIGS. 8 and 9, the thermal control elements are both located on the outer surface of the second (bottom) substrate 114, although various other configurations of locating the thermal control elements may be employed, as taught in application Ser. No. 15/607,940.

Thermal control of various portions of the EWOD device may be combined with droplet manipulation control of different portions of the EWOD device to perform the methods of the present invention. In exemplary embodiments, the control system operates to apply suitable actuation voltages to pertinent array elements in a suitable sequence at a predetermined time, rate, and duration in accordance with a specified or preset duty cycle, and/or based on actual real time sensed properties of the droplet. In this manner, by using intermittent actuation patterns applied to different portions of the EWOD element array, different droplet manipulation operations may be performed at different portions of the EWOD device array. Details of applying intermittent actuation patterns to different portions of the EWOD device array are described, for example, in Applicant's application Ser. No. 15/475,410 filed on Mar. 31, 2017, the content of which also is incorporated here by reference.

Figure 10:
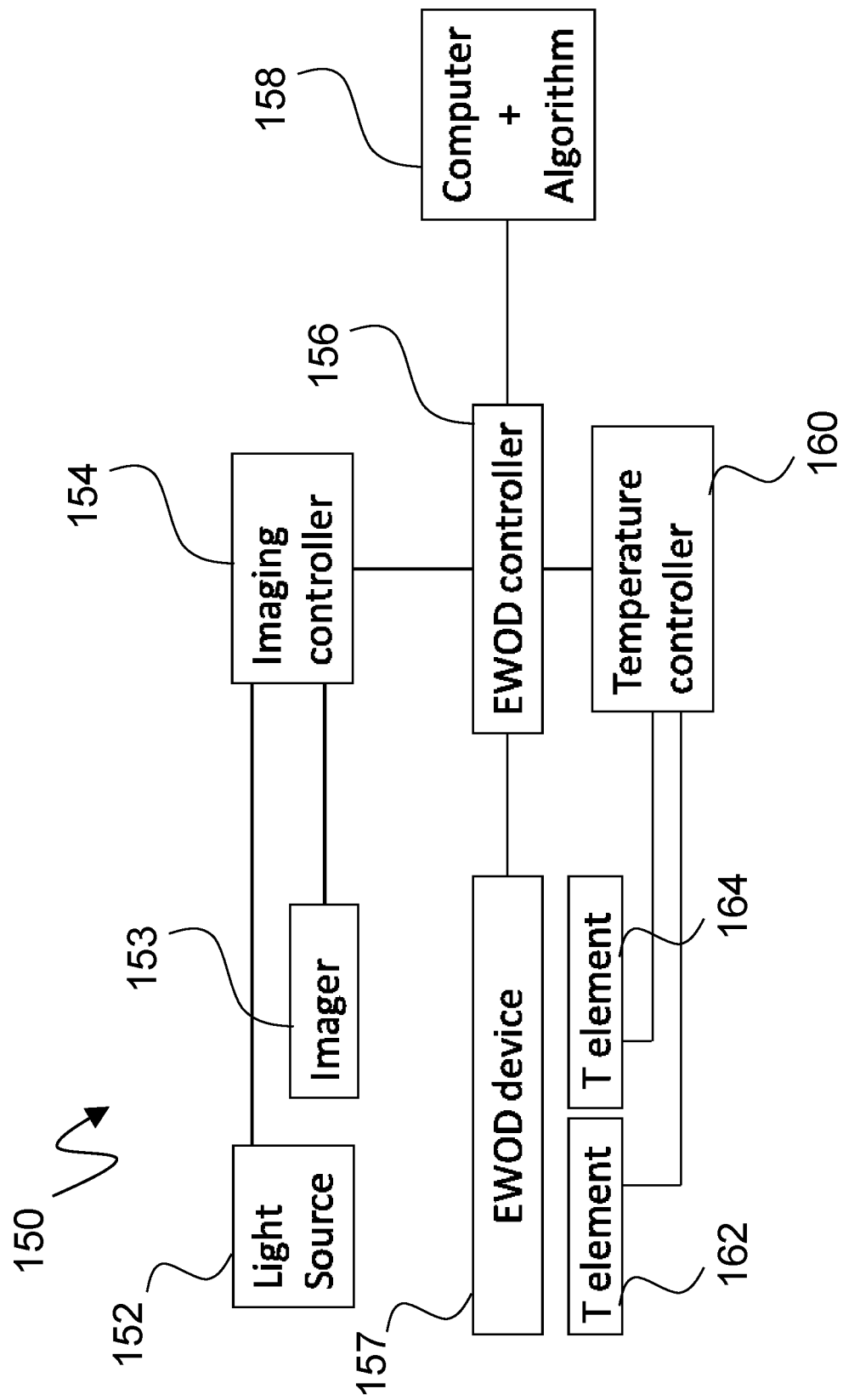
FIG. 10 is a drawing depicting an exemplary microfluidic system in accordance with embodiments of the present invention including thermal control elements and internal and external sensor modules.

FIG. 10 is a drawing depicting an exemplary microfluidic system 150 in accordance with embodiments of the present invention including thermal control elements and internal and external sensor modules. To make the fluorescence measurements, the system 150 may include a light source 152 for emission of the measurement light as referenced above, and an imager 153 that acts as an optical sensor for detecting received light from the reaction droplets for performing the fluorescence measurements as is known in the art. The operation of the light source and imager may be controlled and analyzed by an imaging controller 154.

The light source, imager, and imaging controller may be combined with a microfluidic system to perform the digital biological assay. The microfluidic system may be configured as an EWOD or AM-EWOD based system in accordance with the devices described with respect to FIGS. 2-9 above. For general reference as shown in FIG. 10, the microfluidic system may include an EWOD controller 156 that may be configured comparably as the control system described above, which controls actuation of an array of electrowetting elements incorporated into and EWOD device 157. As part of the control application incorporated into such controller, a computer and algorithm 158 for performing control and sensing operations may be provided and stored within a non-transitory computer readable medium or storage device. The microfluidic system further includes a temperature controller 160 and a plurality of thermal control elements (T-elements). In the depicted example, two thermal control elements 162 and 164 are shown, but again it will be appreciated that any suitable number of a plurality of thermal control elements may be employed in a given device as may be suitable for particular microfluidic operations. The temperature controller 160 contains the control electronics and CPU or processing devices, for controlling the temperature of the thermal control elements to generate different temperature control zones within the EWOD device as referenced above and described in application Ser. No. 15/607,940. In addition, although the imaging controller 154, EWOD controller 156, computer and algorithm 158, and temperature controller 160 are illustrated as separate elements in FIG. 10, it will be appreciated that multiple control components may be combined into a single control system component.

In the exemplary reaction protocols for digital biological assays described below, the following is an example set of parameters associated with the EWOD device configuration and operation. It will be appreciated that the following is illustrative and may be adjusted as would be suitable to particular circumstances of any particular biological assay. A typical EWOD device may have 316×130 TFT pixels, where each TFT pixel is 210 um×210 um and the cell gap is 130 um. This is the equivalent of 41,080 pixels, and thus such an EWOD device can accommodate a maximum volume of ~235 uL of droplets. Usable droplet sizes, for example, may be 1×1, 2×1, 2×2, or 3×3 pixels or comparable, and there may be allotted a gap between droplets of two to three pixels. From these droplet arrangements and the size of the EWOD array, one can then calculate the number of droplets and the volume of each partition associated with the digital biological assay reaction protocol.

The AM-EWOD controller operates to control the environment of the partitions closely to minimize variations in the physical properties of the partitions. The following are exemplary partition properties that may be controlled: temperature of partitions, height of partitions (i.e. distance between the top and bottom of the device), and surfaces with which the partitions are in contact. By rendering volume variations among the partitions negligible, the determined results for the partitions are accurate and easily compared from partition to partition.

Figure 11:
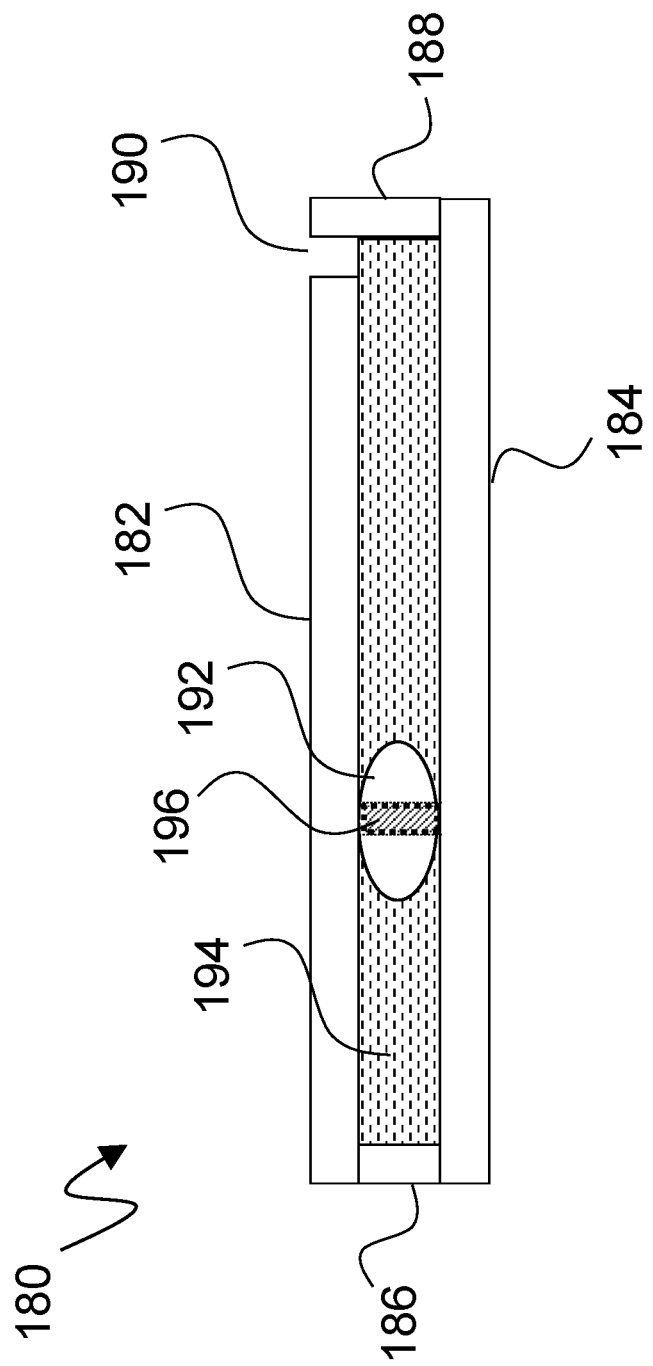
FIG. 11 is a drawing depicting a portion of an exemplary EWOD device, which illustrates the volume of a droplet/partition being assessed for a biological entity initiated new product substance.

This enhanced control means that measured partition properties, such as optical fluorescence measurements or other partition property measurements, are made in essentially a fixed volume of the partition with minimal variations. FIG. 11 is a drawing depicting a portion of an exemplary EWOD device 180, which illustrates the volume of a droplet/partition being assessed for a biological entity initiated new product substance. Similar to previous examples of EWOD devices described above, the EWOD device 180 includes a top substrate 182 and a bottom substrate 184, which are separated by a spacer 186 to define the EWOD channel. A side wall 188 further may define a port 190 for the input of fluid into the EWOD channel. FIG. 11 further depicts a liquid droplet 192, which may constitute a partition for a biological assay, encompassed within a non-polar fluid (oil) 194. With the enhanced control of partition properties of the present invention, optical fluorescence measurements or other partition property measurements are made in essentially fixed volume 196 within the partition 192 with minimal variations among the numerous partitions.

The precise partition volume has enhanced effects for obtaining accurate results for a digital biological assay. When all partitions are essentially identical, standard Poisson statistics can be used to model the distribution of the biological entities in partitions with high accuracy. In contrast, when partition volumes vary in an unpredictable way, then the Poisson model will provide a poor estimate of the original number of biological entities in the sample reservoir. In addition, each partition contains a discrete number of biological entities, and each of these biological entities transforms reagents also present in the partition into a new product substance that can be monitored in real-time by the system by changes in a partition property. The concentration of the new product substance generated by the biological entity, and thus the degree of change to the partition property, will be dependent on the partition volume. A measurement that assesses a particular volume of the partition, such as a point measurement, will depend on the actual volume of the partition, whereas a reference substance added to the bulk sample before partitioning will appear constant. As a result of partition volume variation, partitions with the same number of biological entities will appear to generate the new product substance at different rates, and thus lead to inaccurate results of the biological assay.

Figure 12A:
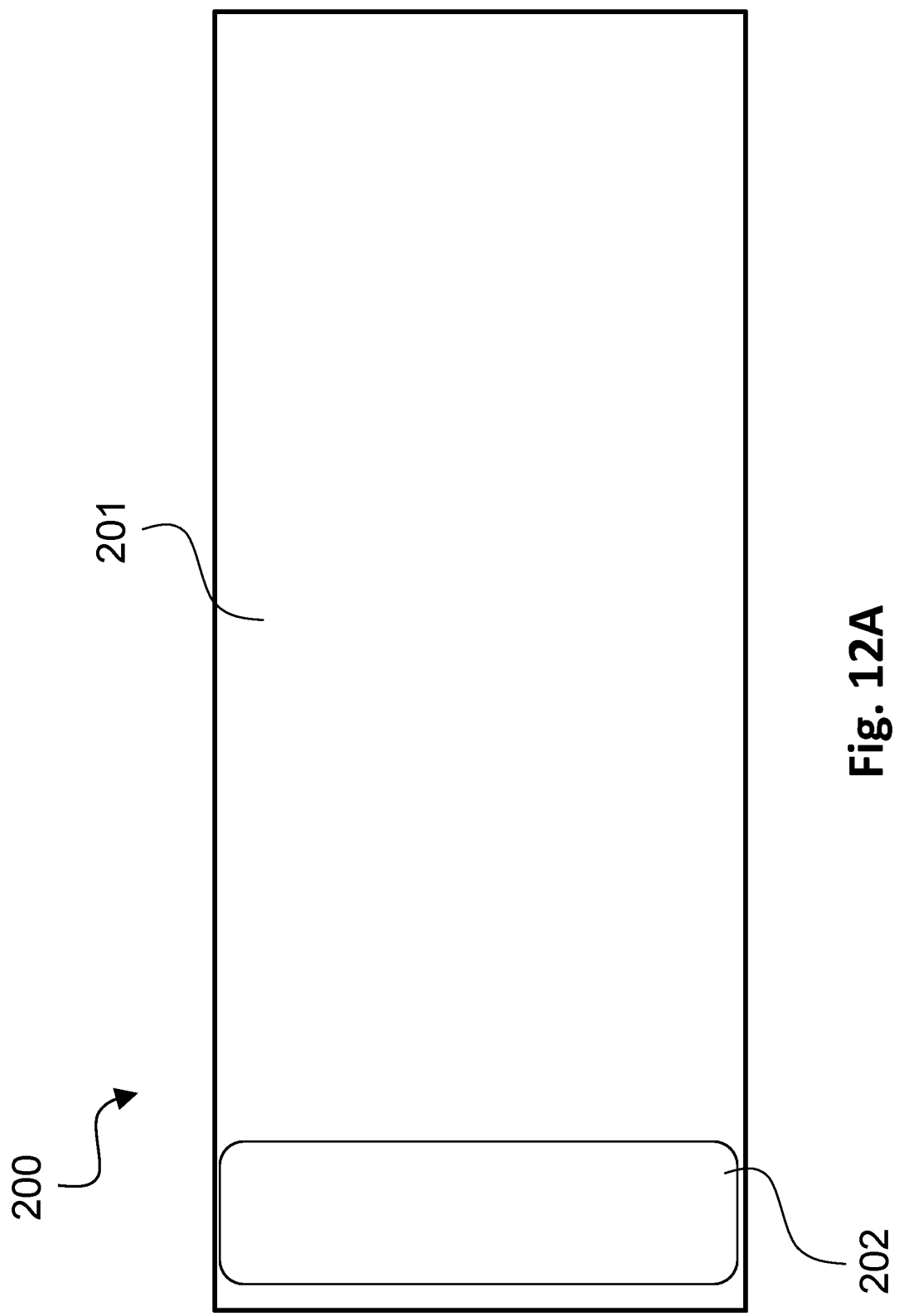

FIGS. 12A-12G are drawings depicting a progression of steps constituting an exemplary method of performing a partitioning process to generate partitions for use in a biological assay reaction protocol, in accordance with embodiments of the present invention. FIG. 12A illustrates an initial preparation of an EWOD cartridge 200 in a simplified fashion for purposes of illustration. It will be appreciated that the EWOD cartridge 200 would have a structure comparable to the embodiments of the EWOD devices described above. As illustrated in FIG. 12A, a sample fluid is loaded onto an EWOD array 201 of the EWOD cartridge 200 to generate a sample reservoir 202 of the sample fluid, containing biological entities and the reagents for a chemical or biochemical reaction. The sample reservoir 202 has a measured or known volume of fluid, and constitutes the sample fluid that contains the biological entities that are the subject of the biological assay. The volume of the sample reservoir is stored by the device control system.

Figure 12B:
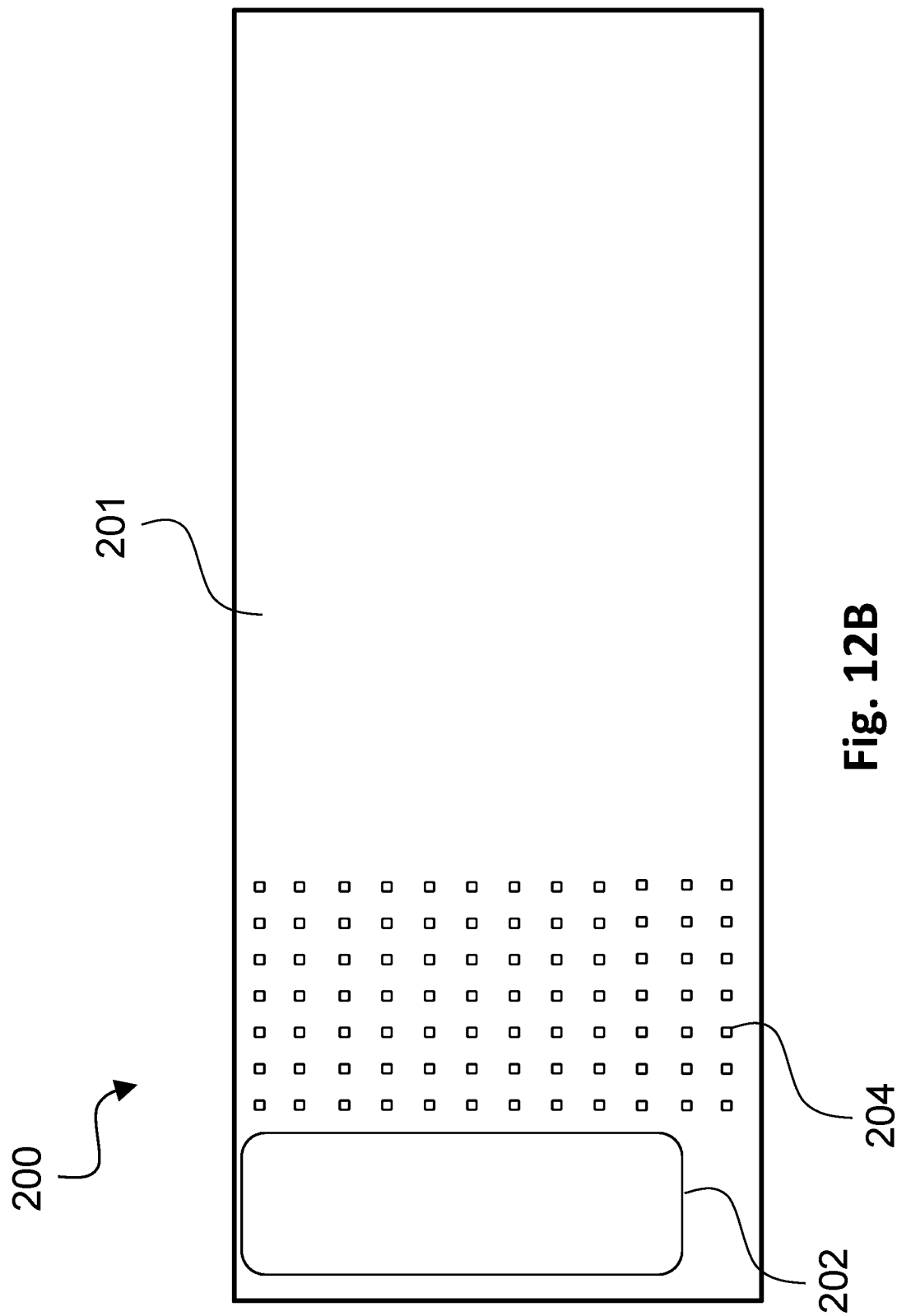
Figure 13:
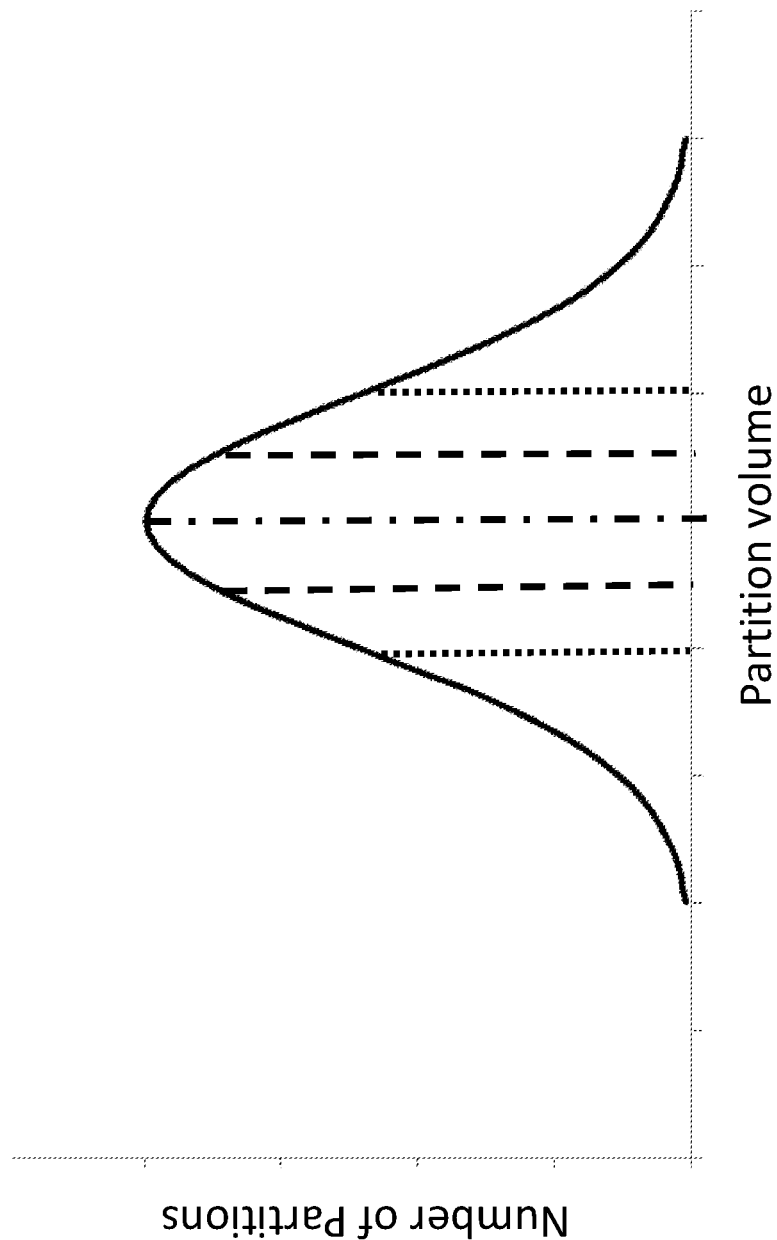
FIG. 13 is a graph depicting a typical distribution of partition size that results from a conventional partitioning process.

In a first step of the reaction protocol as shown in FIG. 12B, the electrowetting operation of the EWOD cartridge 200 is used to pull a plurality of sample droplets 204 from the sample reservoir 202 onto the EWOD array 201. The sample droplets 204 correspond to individual partitions for the biological assay, and some partitions contain biological entities and others do not. In this initial partitioning, about 5% of the biological sample reservoir is divided into a plurality of partitions as illustrated in FIG. 12B. As referenced above, for accuracy of the biological assay, it is desirable that the partitions all have essentially the same volume, although as drawn from the sample reservoir, the partitions in actuality may be the same or different sizes. In this regard, FIG. 13 is a graph depicting a typical distribution of partition size that results from a conventional partitioning process. The center line represents the mean partition volume that may be a target partition volume that is dictated by the device settings and electrowetting operations. Although the center line volume is the mean, the resultant partition volumes typically will be distributed comparably as shown in FIG. 13. The dashed and dotted lines may represent a range of partition volumes relative to the mean. For example, the dashed lines may represent plus/minus a standard deviation variation from the target volume, and the dotted lines, for example, may represent plus/minus a two standard deviation variation from the mean volume.

Figure 12C:
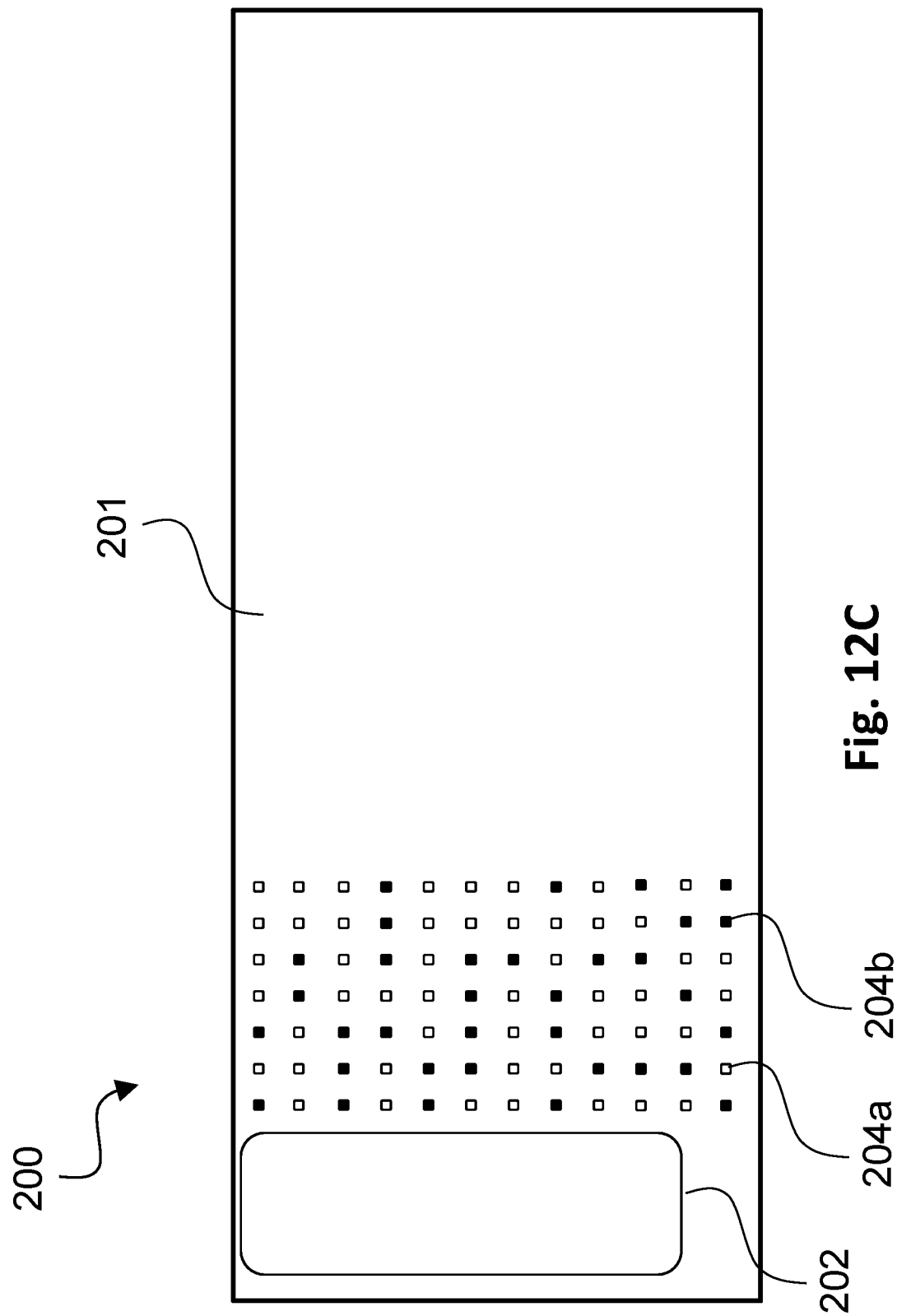

To account for such variation, in a second step of the reaction protocol as shown in FIG. 12C, the AM-EWOD sensing components measure the volumes of the individual partitions. The volumes, for example, may be determined using integrated impedance sensor circuitry integrated within the arrays elements, as described above with respect to FIG. 7. After the volumes have been measured, the volume values are determined by the control system of the microfluidic system, and along with the volume of the sample reservoir from which the droplets were partitioned, are stored within the control system. The control system further may calculate the mean droplet size and the standard deviation for the droplet population, to generate a distribution comparably as described above with respect to FIG. 13. For a given biological assay, an acceptable droplet size variation from the mean may be acceptable, such as for example within a percentage of the mean, such as ±5% or ±10%, or by some other suitable statistical measure such as within a given fraction or number of standard deviations from the mean. For example, ±0.5 standard deviations from the mean may be employed as an acceptable variation range, although any suitable variation parameter may be employed. The control system then identifies partitions with volumes within the acceptable range versus partitions with volumes outside of the acceptable range. In the example of FIG. 12C, for illustration the white partitions 204a constitute partitions determined to be within the acceptable volume range, and the blackened partitions 204b constitute partitions determined to be outside of the acceptable volume range.

Figure 12D:
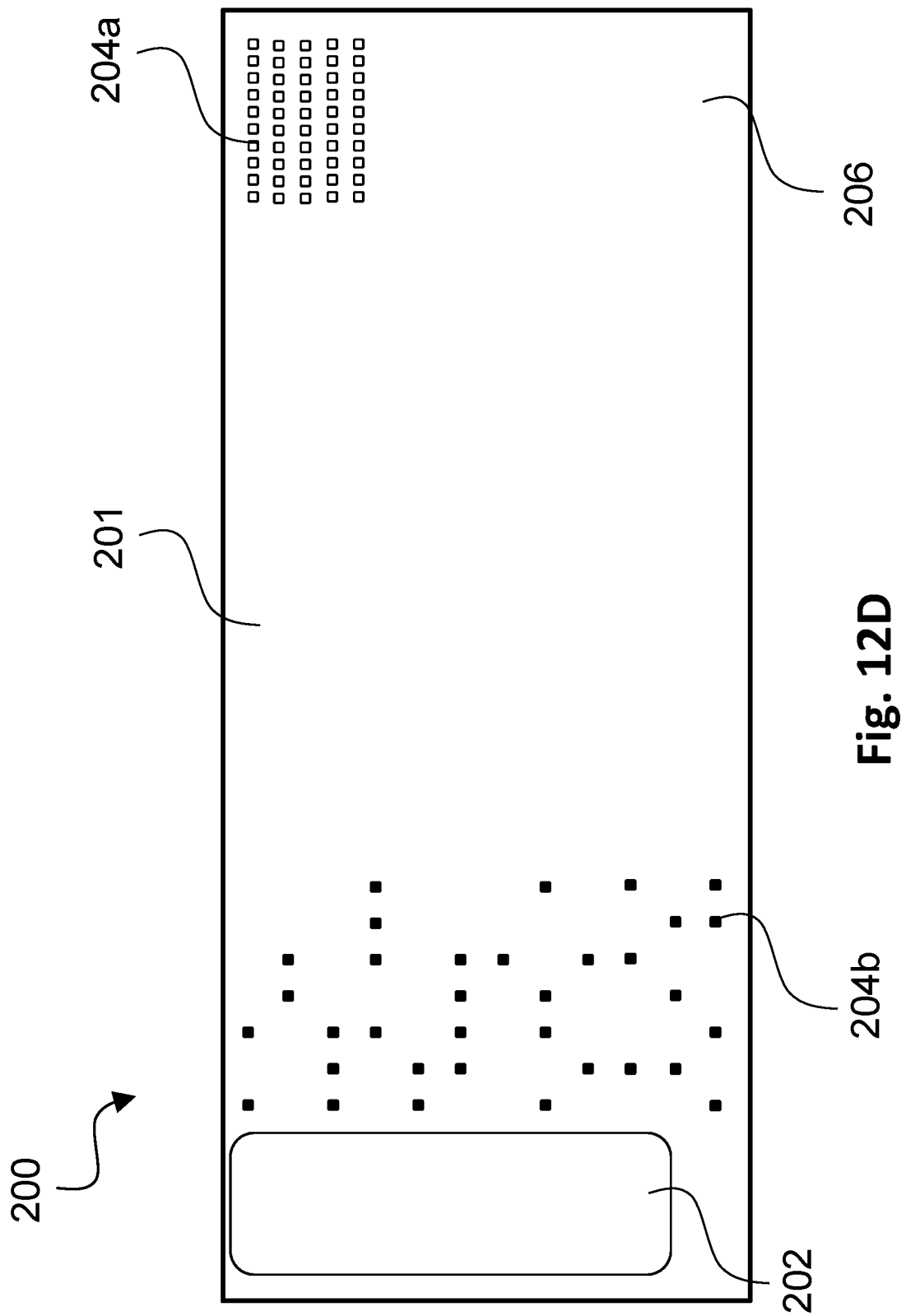
Figure 12F:
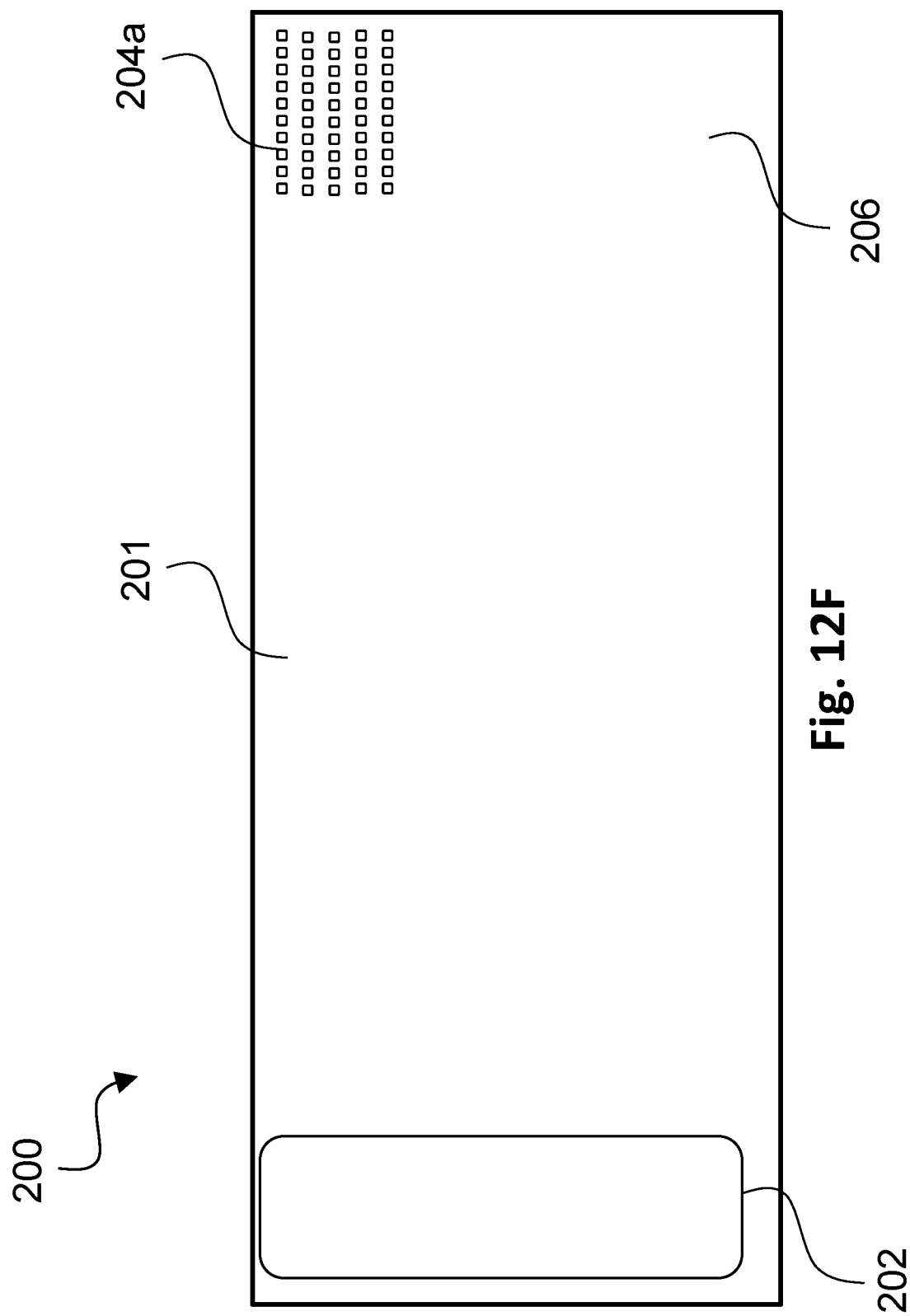

FIGS. 12D-12F illustrate steps to isolate the acceptable partitions 204a for further manipulation to perform the biological assay. As shown in FIG. 12D, the acceptable partitions 204a, i.e., partitions within the set acceptable volume variation range, first are moved by electrowetting operations into an assay region 206 of the EWOD array 201. The open array of partitions is designed to enable rapid automated segregation of partitions that are within the required volume range from the array into which they were partitioned into a new array and location for the biological assay. As shown in FIG. 12E, next the non-acceptable partitions 204b are merged by electrowetting operations into a single return droplet 208. As shown in FIG. 12F, next the return droplet 208 is merged by electrowetting operations back into the original sample reservoir 202.

The operations depicted in FIGS. 12B-12F may be repeated in multiple iterations. For example, a further 5% of the sample reservoir may be partitioned with each iteration. With each iteration, a certain proportion of partitions will be determined to be within the acceptable volume range, and moved into the assay region 206. Any non-acceptable partitions outside of the acceptable volume range will be returned to the sample reservoir. Additional iterations are performed until the sample reservoir has been divided into the desired number of partitions, with all of the partitions having been determined to be within the acceptable volume range. The desired number of acceptable partitions may constitute any requisite portion of the original sample reservoir, and up to the entire sample reservoir may be partitioned in this manner using the multiple iterations.

Figure 12G:
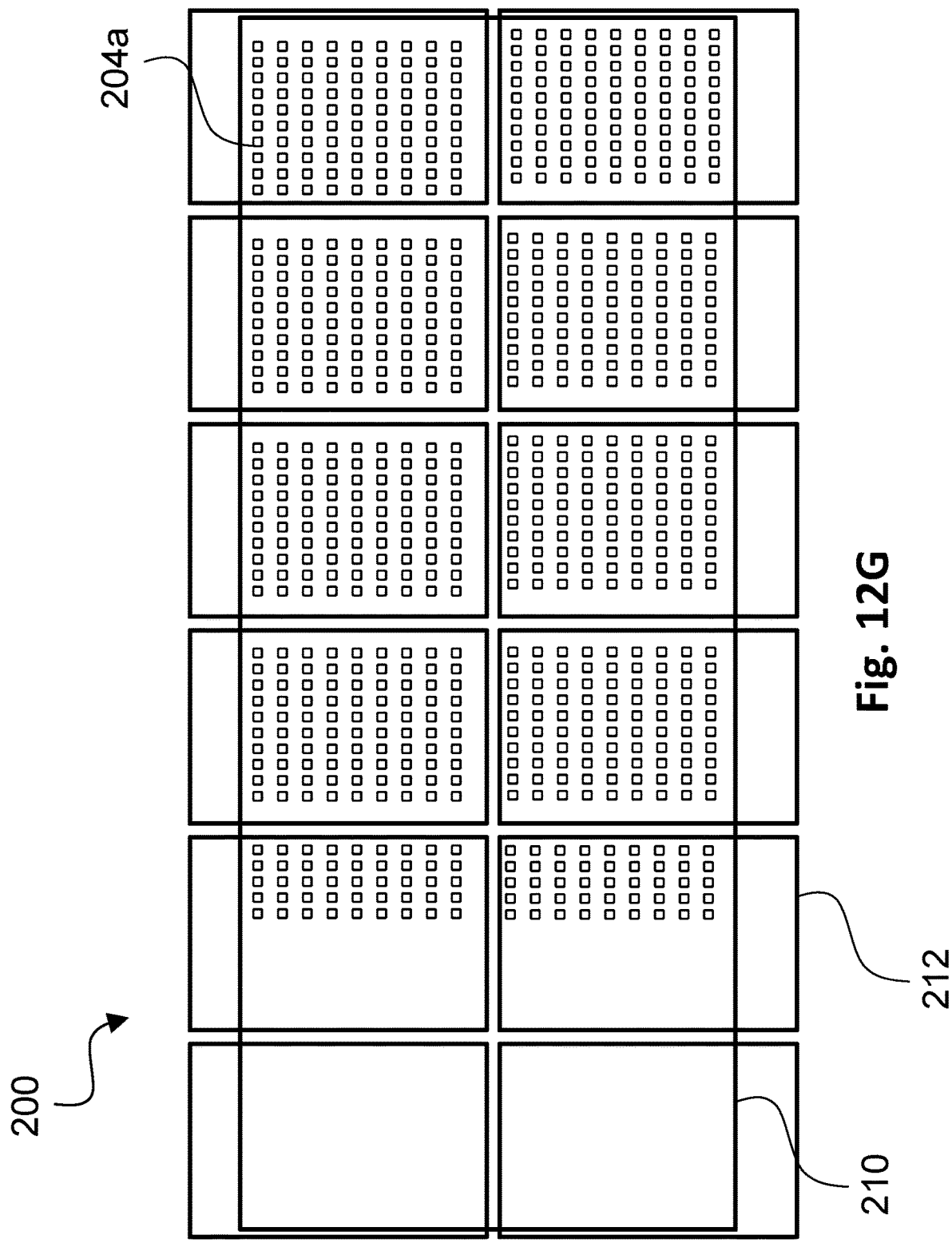

FIG. 12G is a drawing depicting the results of the partitioning process following the requisite number of partitioning iterations. For example, a sample reservoir of an original volume of 20 ul may result in the generation of 800 to 900 partitions that are positioned in an array format comparably as depicted in FIG. 12G. In this example, the EWOD cartridge 200 is depicted as including an array area 210 that contains the array elements of the EWOD device. The array area 210 has dispensed thereon the partitions 204a that were generated as described with respect to FIGS. 12B-12F. The array area 210 further is mounted adjacent to a plurality of thermal control elements 212. In this example, there are twelve thermal control elements, which is suitable for performing a variety of biological assays including nucleic acid amplification by PCR. Any suitable number of thermal control elements may be employed depending upon the biological assay being performed. With such configuration, different zones of the array area corresponding to a respective thermal control element may be subjected to different thermal states for performing different aspects of a biological assay.

Once the sample volume has been partitioned effectively, the microfluidic system may be operated to perform a biological assay. The biological assay may be initiated by performing an operation to change the environment of the partitions, which initiates a biological process to be performed by the biological entities. The environmental change may constitute, for example, a change in temperature, the addition of an extra chemical component, light activation, electrochemical activation, or other method that can initiate a biological process to be performed by the biological entities. In other words, the environmental change initiates a biological process by any biological entities that are present within a partition, which alters a property of that partition that can then be measured. For example, the partition property may be an optical property, such as fluorescence or absorption of the partition, or a chemical-based property such as for example a change in electrochemical behaviour, pH, or some other physical property. Typically, the change in the partition property results from the creation of a new product substance that is generated by the biological process in response to the environmental change. The degree of effect on the partition property is therefore related to a concentration of the new product substance, which in turn is related to a number of biological entities present within the partition being measured.

As part of the biological assay, the system measures the volume of all partitions with respect to time and in real time, and measures the applicable partition property with respect to time and in real time. From such measurements, the system calculates the relative concentrations of the new product substance in the partitions that are created by the biological entity process, and adjusts them according to the measured partition volumes. By accounting for variations in partition volume during the enhanced partitioning process, and by continuing to measure partition volume in real time during the biological assay, the output is corrected for any changes in partition volumes that occur either during partitioning itself, or otherwise during the biological assay.

Using the methods of the present invention, the microfluidic system records a full partition history, and for each partition the following are known:
1. The volume of the reservoir from which the partitions were generated.
2. The order in which the partitions were generated from the reservoir.
3. The volume of each partition over time during the biological assay.

As described above, each partition contains a discrete number of biological entities (which can be zero). In addition, all partitions contain the reagents necessary for a biochemical or chemical reaction that is initiated by the biological entity. These reagents are present at a much higher concentration than the biological entity, and are therefore present in all partitions at essentially the same concentration. After partitioning, the environment of the partitions is changed as described above, and the biological entity or entities initiate the biological process that transforms the reagents present in the partition into the new product substance. The presence of the new product substance in the partition causes a change in the applicable partition property, such as for example fluorescence, absorption, electrochemical behavior, pH, or other physical property. The change in the partition property and the partition volume are monitored with respect to time in real time during the biological assay.

Figure 14B:
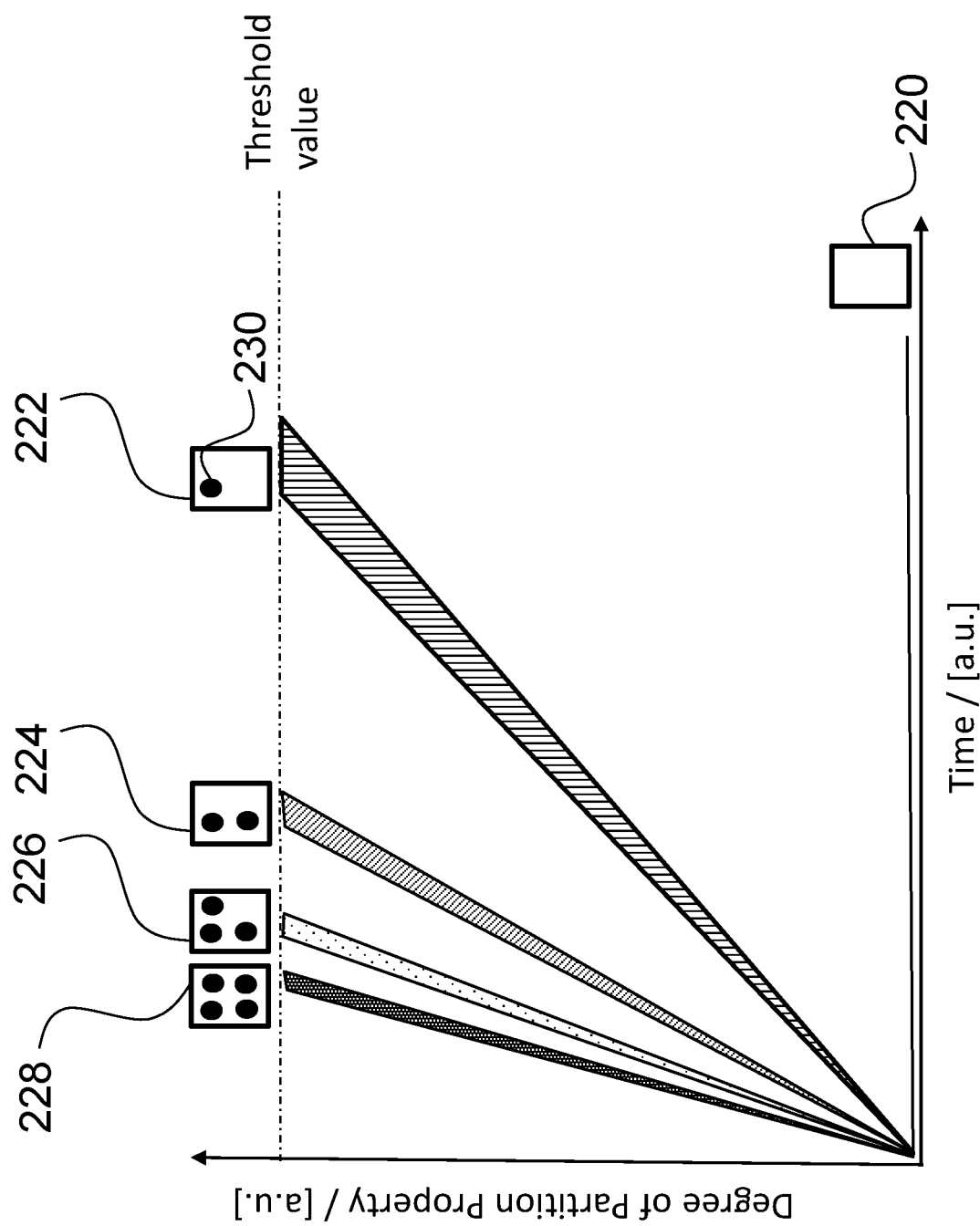

FIGS. 14A-14C illustrate the advantages of the present invention. In these figures, the degree of the partition property is plotted as a function of time of the assay for different ranges of partition volume variation. This is plotted for partitions 220, 222, 224, 226, and 228, which in this example respectively include 0, 1, 2, 3, and 4 target biological entities 230. Since there can only be discrete numbers of biological entities per partition, only certain line gradient values are observed.

Referring to FIG. 14A, as partition 220 has zero biological entities, the measured degree of the biological entity dependent partition property remains at zero. For non-zero partitions, the degree of the partition property depends upon two features: (1) the number of biological entities, and (2) the volume of the partition. In this regard, for a given number of biological entities in a partition, and within a given time, the degree of the partition property will be greater when the partition volume is relatively small, as a larger partition volume dilutes the effect of the biological entity dependent partition property. As referenced above, the behavior of the partition property tends to be related to the concentration of the new product substance generated by the biological process of the biological entities. Accordingly, a degree of the observed partition property (e.g., fluorescence, chemical change) builds more rapidly due to the smaller partition size, as the concentration of the new product substance will be greater within a given amount of time. Accordingly, in FIG. 14A a steeper slope of the relationship represents a more rapid effect of the partition property. The slope is steeper, therefore, for a partition having a larger number of biological entities, and for a partition of a smaller volume which will have a higher concentration of the new product substance within a given time.

The shaded regions in FIG. 14A represent the range of the degree of the partition property over a volume variation of the partitions. In the example of FIG. 14A, the variation range is ±10% relative to a mean partition volume. In the figure, therefore, for a given partition 222, 224, 226, or 228, the left side of the shaded region is a gradient value plot of the partition property for the low end of the volume range, and the right side of the shaded region is a gradient value plot of the partition property for the high end of the volume range, with the shaded region encompassing gradient values for the partition property over the entire volume variation range of ±10% relative to a mean partition volume.

As seen in FIG. 14A, over short time periods it is difficult to ascertain differences between the partitions containing one or more biological entities, and it particularly is difficult to ascertain partitions having relatively larger numbers of biological entities such as three versus four. In other words, during shorter time periods two or more of the shaded regions may overlap, meaning that a given concentration of new product substance affects the partition property to a degree that cannot be conclusively associated with a specific number of biological entities within a partition. This renders it difficult to provide an accurate count of the total number of biological entities, as certain partitions may be misclassified as to the number of biological entities. One option is to lengthen the time of the biological assay so that the plots become more distinguishable from each other, but lengthening assay time often is an undesirable solution. In addition, the biological entity initiated reaction will stop when all the reagents in the partition have been consumed. At this point all partitions will assume the same output independent of the number of biological entities in partitions.

Instead, the partitioning process described above reduces, and can nearly eliminate, the volume variation among the partitions. In this regard, FIG. 14B is comparable to FIG. 14A, except the plots of the partition property are based on a volume variation range of ±5% relative to a mean partition volume. FIG. 14C also is comparable to FIG. 14A, except the plots of the partition property are based on an optimum partitioning in which the volume variation range is essentially zero. As seen in FIGS. 14B and 14C, a substantial to near complete reduction of the partition volume variation enhances the ability to ascertain partitions having different numbers of biological entities in very short time periods, particularly for the relatively larger number of biological entities as to which the partitions generally are more difficult to ascertain. As a result, by reducing or eliminating volume variation effects by partitioning in accordance with embodiments of the present invention, a more accurate biological assay result can be achieved in a shorter amount of time.

The enhanced partitioning process described above thus may be combined with real-time measurement of partition volume during the biological assay. Integrating real-time measurement of partition volume within an AM-EWOD system for automated partition manipulation has several advantages over conventional configurations. The described partitioning process generates a suitable size distribution of partitions for a particular biological digital assay. The system assesses the partition size distribution for a population of partitions after partitioning, and uses this information to automate the selection of partitions within a particular size range and the repartitioning of partitions with sizes outside the required size range.

In digital biological assays for assessing individual enzyme (biological entity) activity, accurately knowing the partition volume when assessing individual enzyme properties enables any partition size induced variation in the concentration of an enzyme initiated substance to be corrected. The rates of formation of the enzyme initiated substance will then reflect differences in individual enzyme activities, and hence an assessment of the heterogeneity of an enzyme sample. Similarly, accurately knowing the partition volume when assessing the properties of individual cells enables better analysis of the degree of heterogeneity in a population of cells.

Another advantage is enhanced counting of biological entities and assessing sample concentration with digital biological assays. From the volume corrected real-time analysis of the change in concentration of the biological entity initiated substance per partition, it is possible to distinguish between partitions that originally contained 0, 1, 2, 3 or 4 or even 5 biological entities. For mean biological entity partition concentrations <1, counting the total number of biological entities in all the partitions and dividing by the total sample volume gives a good estimate of the original sample concentration. For higher concentration samples, it could be more appropriate to combine this counting method with a modified Poisson analysis for the partitions containing greater than 4 biological entities per partition to determine the original sample concentration. For example, for digital biological assays such as for qPCR, comparing the time courses for partitions containing 1, 2, 3, or 4 copies of target DNA allows an assessment of the efficiency of the PCR process.

For biological assays more generally, partition volume changes can occur for a variety of reasons during performance of the biological assay, and the real-time measurements permit correcting for any such volume variations. For example, real-time measurement of partition size enables merged partitions to be better accounted for in the assessment of the output of a digital biological assay. Real-time measurement of partition size further enables accounting for changes in partition size caused by, for example, evaporation of water from partitions over the course of a digital biological assay, and such variations can be assessed and incorporated into the assay analysis. Real-time measurement of partition size further enables partitions in which other non-biological entity initiated changes in partition property occur that show a different time course, from being included in the assessment of the output from the digital biological assay. The described system, therefore automatically: integrates and automates measuring the sample volume; generates and measures the volumes of the sample partitions; initiates a biological entity driven process; monitors partition volume and the biological entity initiated partition property; and uses this information about each partition to more accurately determine the relative time dependent changes in the partition property, thereby increasing the ease and accuracy with which a digital biological assay is carried out.

An aspect of the invention, therefore, is a method of performing a biological assay that employs a partitioning process that limits variation in partition volume, and monitors the partition volume and partition property in real-time, thereby enhancing the results of the assay. In exemplary embodiments, the method may include the following steps:

1. Load the sample reservoir containing biological entities onto the AM-EWOD device.
2. Measure the volume of the sample reservoir.
3. Divide some of the sample reservoir into partitions, wherein some partitions will contain biological entities and others will not.
4. Measure the volumes of each partition after they are prepared, and the volume of the sample remaining in the sample reservoir from which the partitions were generated.
5. Calculate the mean volume and standard deviation or standard error of the partitions, and set an acceptable volume range for the partitions.
6. Move partitions with volumes within the acceptable range to a specified location on the AM-EWOD element array to form an array of partitions within the acceptable range.
7. Merge the partitions with sizes outside of the acceptable range and return such partitions to the sample reservoir for repartitioning.
8. Repeat steps 3 to 7 until all or a sufficient portion of the sample reservoir has been partitioned.
9. Start a biological process by changing the environment associated with the AM-EWOD device, such as for example by a change in temperature, the addition of an extra chemical component, light activation, electrochemical activation, or other method.
10. Measure the volume of all partitions with respect to time and in real time during the assay.
11. Measure a selected one or more biological entity dependent partition property with respect to time and in real time, which is indicative of a concentration of a new product substance that is generated from the biological process.
12. Calculate the relative concentrations of the new product substance in the partitions and adjust them according to the measured partition volumes.
13. Plot the time dependent changes in relative concentrations of the new product substance for the partitions.
14. Calculate the relative rates of the new product substance's formation for each partition.
15. Group the partitions according to the rate of formation of the new product substance.
16. Categorize partitions as follows: deeming partitions that show no change in the partition property as having zero biological entities; deeming those partitions with a slowest rate of increase of the partition property as having one biological entity; deeming those partitions with a next slowest rate of increase of the partition property as having two biological entities; deeming those partitions with a next slowest rate of increase of the partition property as having three biological entities; and deeming those partitions with a next slowest rate of increase of the partition property as having four or more biological entities.

In this manner, correcting for the partition volumes greatly simplifies identification of partitions that contain up to 1, 2, 3 or 4 biological entities, as illustrated in a comparison of FIGS. 14A-14C above.

In the previous examples, the generation of the partition property varies linearly with respect to time. In alternative embodiments, the partition property may experience an exponential increase with time. Examples of biological assays that show exponential increases in the partition property include DNA polymerase chain reaction and isothermal nucleic acid amplification. In these assays, the biological entity is copied during the biological process, and a probe or intercalating fluorescent dye is used to readout the concentration of the biological entity.

Figure 15B:
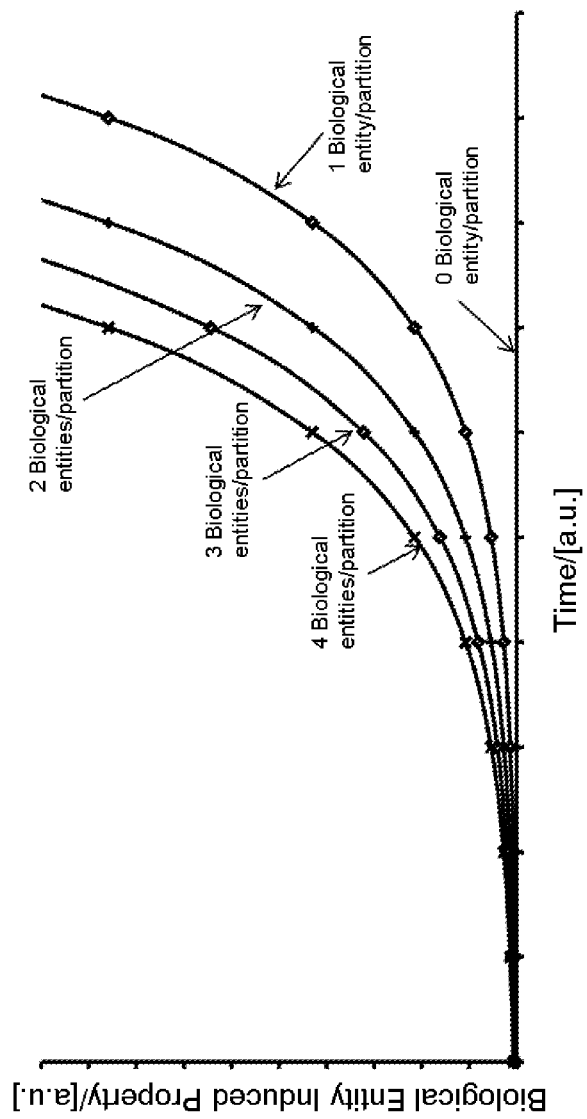

FIGS. 15A and 15B are graphs depicting the degree of the partition property plotted as a function of time of a biological assay for different ranges of partition volume variation, for a partition property that varies exponentially with time. Referring first to FIG. 15A, the solid lines illustrate the mean change in the partition property with respect to time, and the dotted lines illustrate the outcome for partitions that have volumes that are 10% smaller (steeper gradient) and 10% larger (less steep gradient) relative to the mean. Similarly as with the linear partition properties, at the shorter times it is difficult to distinguish among partitions of different numbers of biological entities, particularly with respect to the larger numbers such as 3 versus 4 biological entities. FIG. 15B is a comparable graph as FIG. 15A, but with the partition volumes being accounted for in accordance with embodiments of the present invention. With the enhanced partitioning and related processing including real-time volume monitoring, partitions of different numbers of biological entities are readily distinguished even for the larger numbers of biological entities.

The shape of these curves is dependent on the efficiency of the amplification process, and when the efficiencies are similar the curves cross a threshold value (see FIG. 15A in particular) for measuring the partition property that is dependent on the initial number of biological entities in the sample. The exponential curves may then be compared by considering the time that it takes for the output from the partition to reach this threshold level. This method is commonly used in PCR to assess the relative concentrations of samples. The threshold is often taken as between 3 and 10 times noise associated with negative partitions, and is illustrated in FIG. 15A. After correcting for partition size, the partitions are categorized relative to the partitions that take longest to reach the threshold. The partitions are then assigned as having contained initially 0, 1, 2, 3, 4, and more copies of the biological entity as shown in the enhanced results of FIG. 15B.

Embodiments of the present invention are not limited to reactions that are zeroth order (linear) reactions and exponential reactions, as described above. Rather, the invention may be used to compare relative rates of formation of a new product substance based on a measured partition property even when the kinetics of the particular chemical reaction are not fully understood. Time courses may be used to estimate the concentration of the original biological sample for any type of reaction relationship.

For example, for an initial sample concentration of, on average, approximately one biological entity per partition, Poisson statistics predict that the percentage of partitions containing >/=5 biological entities is about 0.2%. The current invention describes a system and method to categorize partitions according to the initial number of biological entities that they contain. In one aspect of the invention the process differentiates between partitions that contained 0, 1, 2, 3, 4 and >4 biological entities. Under these circumstances it is useful to estimate the original number of biological entities in the sample simply by summing the number of partitions containing a particular number of biological entities, and multiplying by the number of biological entities per partition. The original sample concentration is obtained by dividing the total number of counted biological entities by the initial sample volume. Very few partitions will contain >5 biological entities when the initial sample concentration results in one biological entity being the probabilistic number in each partition.

Figure 16:
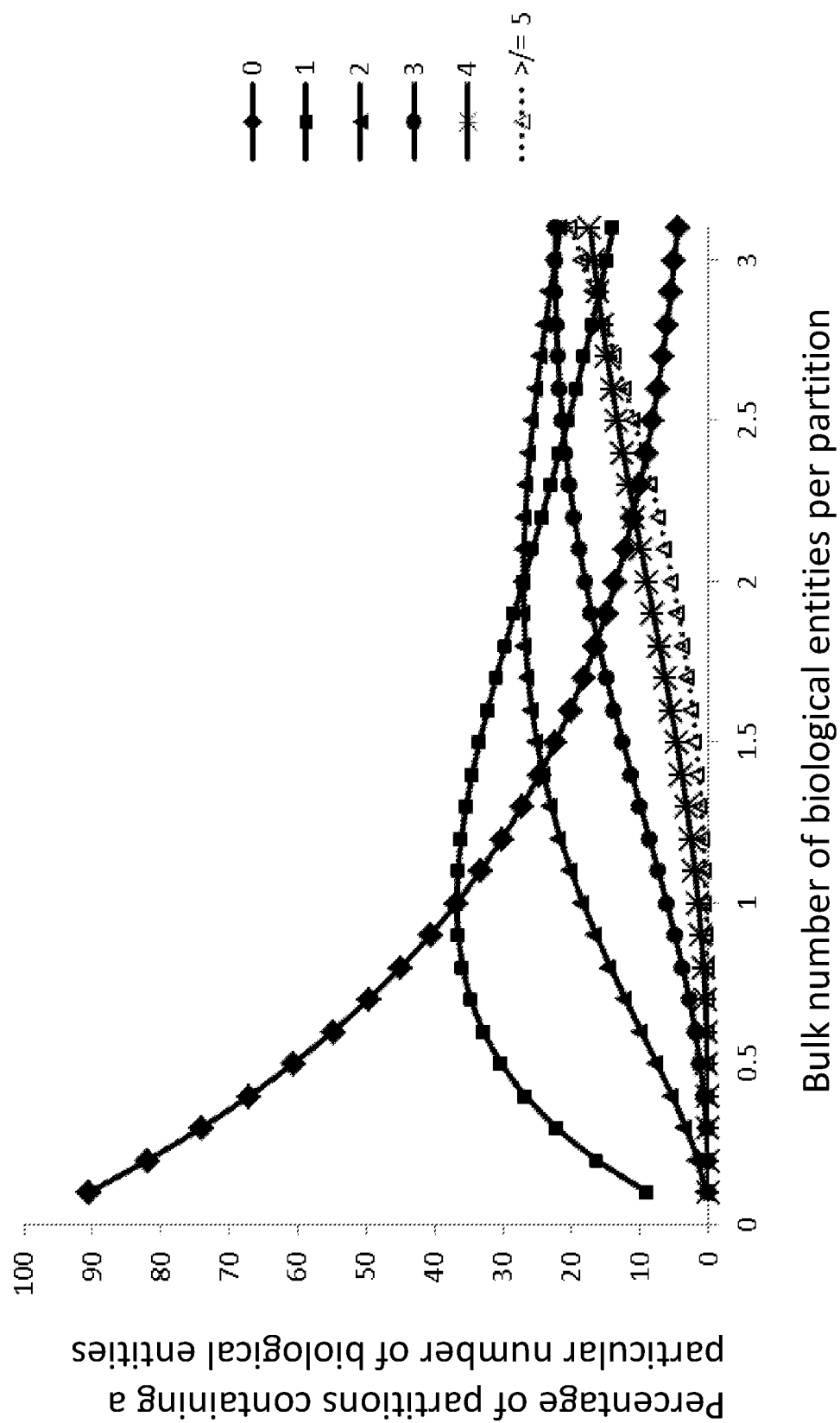
FIG. 16 is a graph depicting the number of partitions estimated to contain 0, 1, 2, 3, 4 initial copies of biological entities relative to the bulk concentration of biological entities per partition, according to Poisson statistics.

FIG. 16 is a graph depicting the number of partitions estimated to contain 0, 1, 2, 3, 4 initial copies of biological entities relative to the bulk concentration of biological entities per partition, according to Poisson statistics. For a higher mean number of biological entities per partition, i.e. >1 per partition where the number of partitions containing >/=5 biological entities is >0.2% (FIG. 16 open triangles and dotted line), it would be more appropriate to take longer over the initial partitioning and narrow the distribution of partition sizes to the required value +/−5% or less, and then carry out the digital biological assay as described in the previous analysis. A modified Poisson analysis that takes into account the partition volumes and includes analysis of partitions that originally contained 0, 1, >/=2, or 0, 1, 2, >/=3, or 0, 1, 2, 3, >/=4, or 1, 2, 3, 4, >/=5, which could then be used to count the number of biological entities in the original sample and calculate the concentration of the original sample by dividing this by volume of the reservoir.

In another aspect of this invention, the output of the digital biological assay may be an assessment of the individual activities of the biological entities in a sample. For a mean concentration of less than about 0.6 biological entities per partition, Poisson statistics estimates that <10% of partitions will contain >1 biological entity per partition (see FIG. 16). The current invention provides a method to correct the concentration of a new product substance by measuring the partition property, accounting for any differences in partition volume. The time dependent change in the partition property observed for partitions containing one biological entity may then be compared to assess the heterogeneity of the population of biological entities. This, for example, may be used for an enzyme sample or a population of cells.

In another aspect of the invention, the initial partitioning may result in partition volumes that are within the required volume range with no need to repartition. In other words, the number of iterations of the partitioning process is one, and subsequent iterations of the partitioning process are not required. Without the re-partitioning step of multiple iterations, the time taken to prepare the sample for a digital biological assay will be reduced. The biological digital assay may then be carried out as described in the previous embodiments. Similarly, under some circumstances the variation in partition volume in the initial partitioning may be acceptable, for example when a digital biological assay is being carried out where the primary output from the assay is an assessment of the relative activities of individual enzymes in a sample of enzymes. Under such circumstances as well, the number of required iterations is one. Then at a mean concentration of biological entities in a partition of <0.6, most partitions are either empty or contain a single biological entity. Real-time measurement of partition size and the partition property will enable the signal recorded for the partition property to be corrected for any variation in partition size.

During the course of a biological digital assay, two or more partitions may merge generating a resultant partition with a larger volume. In the absence of real-time partition volume evaluation during the biological assay, a larger partition that is formed from two or more partitions merging may appear to have the same partition property over the assay as an unmerged droplet, and yet account for more of the original sample volume. In other words, with merging of partitions, a number of biological entities in the original partitions may not be distinguishable due to the change in volume of the partition by the merging. Possible options include:

Alternatively, in digital biological assays some partitions may have an unusually high value for the partition property, which remains constant throughout the biological entity initiated chemical reaction. In a traditional digital assay, these partitions would be mis-categorized as positive partitions. With real time measurement of the biological entity induced property and partition size in accordance with embodiments of the present invention, this error may be corrected and a partition correctly categorized as negative.

In another aspect of the invention, the number of partitions reaching a threshold value of the partition property for a digital biological assay is assessed in real time. When the rate of partitions reaching the threshold value of the partition property falls to zero, the digital biological assay may be stopped, after which the partitions are categorized by count-

| Partition 1 (no. biological entities/ partition) | Partition 2 (no. biological entities/ partition) | Merged partitions (no. biological entities/new partition) | Standard digital readout with endpoint analysis (no. of droplet/s × no. of biological entities) | Standard digital readout taking into account partition size with end point analysis (no. of droplet/s × no. of biological entities) | Standard digital readout taking into account partition size and real time analysis of partition property (no. biological entities/ new partition) |
|---|---|---|---|---|---|
| 0 | 0 | 0 | 1 × 0 | 2 × 0 | 0 |
| 0 | 1 | 1 | 1 × 1 | 2 × 1 or 1 × 0 and 1 × 1 | 1 |
| 0 | 2 | 2 | 1 × 1 | 2 × 1 or 1 × 0 and 1 × 1 | 2 |
| 0 | 3 | 3 | 1 × 1 | 2 × 1 or 1 × 0 and 1 × 1 | 3 |
| 0 | 4 | 4 | 1 × 1 | 2 × 1 or 1 × 0 and 1 × 1 | 4 |
| 1 | 1 | 2 | 1 × 1 | 2 × 1 or 1 × 0 and 1 × 1 | 2 |
| 1 | 2 | 3 | 1 × 1 | 2 × 1 or 1 × 0 and 1 × 1 | 3 |
| 1 | 3 | 4 | 1 × 1 | 2 × 1 or 1 × 0 and 1 × 1 | 4 |
| 1 | 4 | 5 | 1 × 1 | 2 × 1 or 1 × 0 and 1 × 1 | 5 |
| 2 | 2 | 4 | 1 × 1 | 2 × 1 or 1 × 0 and 1 × 1 | 4 |
| 2 | 3 | 5 | 1 × 1 | 2 × 1 or 1 × 0 and 1 × 1 | 5 |
| 2 | 4 | 6 | 1 × 1 | 2 × 1 or 1 × 0 and 1 × 1 | 6 |
| 3 | 3 | 6 | 1 × 1 | 2 × 1 or 1 × 0 and 1 × 1 | 6 |
| 3 | 4 | 7 | 1 × 1 | 2 × 1 or 1 × 0 and 1 × 1 | 7 |

The most accurate description of number of partitions and partition contents is obtained using real-time analysis of partition volume and the partition property (far right hand column of the above table). Measuring the partition volume at the beginning and end of the assay allows the number of partitions to be accurately determined. However, only with real-time analysis of the partition property can the number of biological entities in a merged droplet be easily estimated and therefore used in the analysis of the original number of biological entities in the sample.

Figure 17:
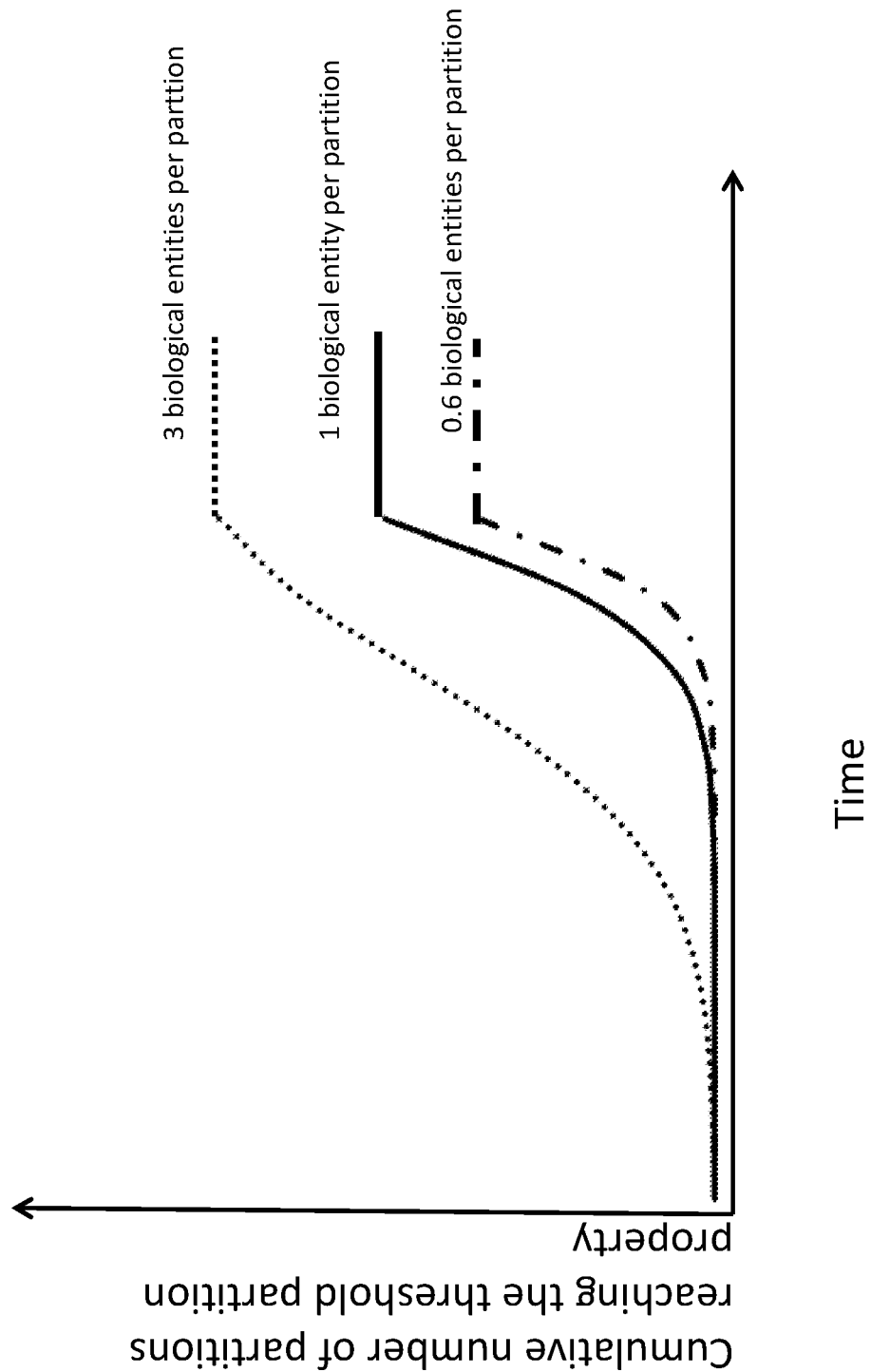
FIG. 17 is a graph that depicts the cumulative number of partitions that have reached a threshold value of a partition property over time.

In digital biological assays a partition may show little change in the partition property. Hence, in a traditional digital assay a partition that exhibits little change has a high probability of being included as a negative partition. An inspection of the partition property and partition volume data in real time in accordance with embodiments of the present invention would detect a clear change in partition property that occurs, which corresponds to the partition containing 1, 2, 3, or 4 (or more) biological entities. These partitions may then be placed in the correct category enabling better analysis of the sample composition.

ing number of biological entities, and an estimate of the initial concentration of the biological entities in the sample reservoir is made. In this manner, the assay time is reduced by stopping the digital biological assay as soon as enough information has been collected to quantify the number of biological entities in the sample. FIG. 17 is a graph that depicts the cumulative number of partitions that have reached the threshold value of the partition property over time. The shape of the curve is dependent on the distribution of biological entities in the partitions. The dotted line corresponds to a sample that initially contained a mean of 3 biological entities per partition, the solid line corresponds to a sample that initially contained a mean of 1 biological entity per partition, and the dashed-dotted line corresponds to a sample that initially contained a mean of 0.6 biological entities per partition. The biological assay may be stopped when the curves reach the plateau, as all biological entities in the partitions would have reach the appropriate threshold value. In other words, the rate at which partitions reach the threshold value becomes zero (horizontal) as all the partitions that contain biological entities have reached the threshold value of the partition property.

In another aspect of the invention, the sample of biological entities may be a library of DNA molecules for next generation sequencing, and the described methods may be used to characterize the distribution of lengths of DNA in such a sample. The library may contain a range of lengths of DNA molecules suitable for next generation sequencing. Part of the sample is partitioned, and the size distribution of partitions is narrowed as described with respect to previous embodiments.

On dilution and partitioning, each partition contains either one DNA molecule or zero DNA molecules, and an excess of reagents needed for DNA amplification by PCR. A concentration regime is chosen such that partitions contain on average zero or one DNA molecule. DNA amplification is initiated by an increase in temperature and the activation of a DNA polymerase enzyme. Real time DNA concentration monitoring is carried out via fluorescence analysis with an intercalating dye. The dye binds tightly to double stranded DNA, and the number of dyes bound depends on the length of the original DNA molecule. After correcting the fluorescence output for partition volume differences, the output can then be assumed to relate to differences in template DNA lengths. Partitions containing longer DNA fragments will reach the threshold value sooner than shorter lengths of DNA. Plotting the time it takes for a partition to reach the threshold value (after taking into account variation in partitions size) will give an estimate of the distribution of lengths of DNA in the next generation DNA sequencing library. This provides a convenient way to analyze the distribution of lengths of DNA in a library for NGS.

In another aspect of the invention, part of the sample reservoir is partitioned, and the size distribution of partitions is narrowed as described in connection with previous embodiments. The digital biological assay is then initiated for these partitions, and the remaining portion of the sample reservoir is maintained under conditions such that the biological process is not initiated for such portion. The sizes of the partitions and the partition property are measured in real time and volume corrected time courses for the change in the property of each partition generated. Partitions are categorized according to the number of biological entities, and an estimate of the total number of biological entities is made using a modified Poisson analysis incorporating information on the number of partitions containing at least 0, 1, and >1 biological entities, but more preferably incorporating information on the number of partitions containing 0, 1, 2, 3, 4 and >4 biological entities. For samples estimated to contain a mean number of about 3 biological entities per partition, the AM-EWOD system can be programmed to partition the remaining sample into smaller partitions such that the mean number of biological entities per partition is <3, which improves the counting as the number of biological entities in each partition is more readily distinguished (as illustrated for example in FIGS. 15 and 16). Alternatively, the sample reservoir may be diluted with a diluent that contains all the reagents for the digital biological reaction being carried out, before automatically partitioning and carrying out the digital biological assay as described in connection with previous embodiments to achieve a mean number of biological entities per partition that is <3.

Figure 18A:
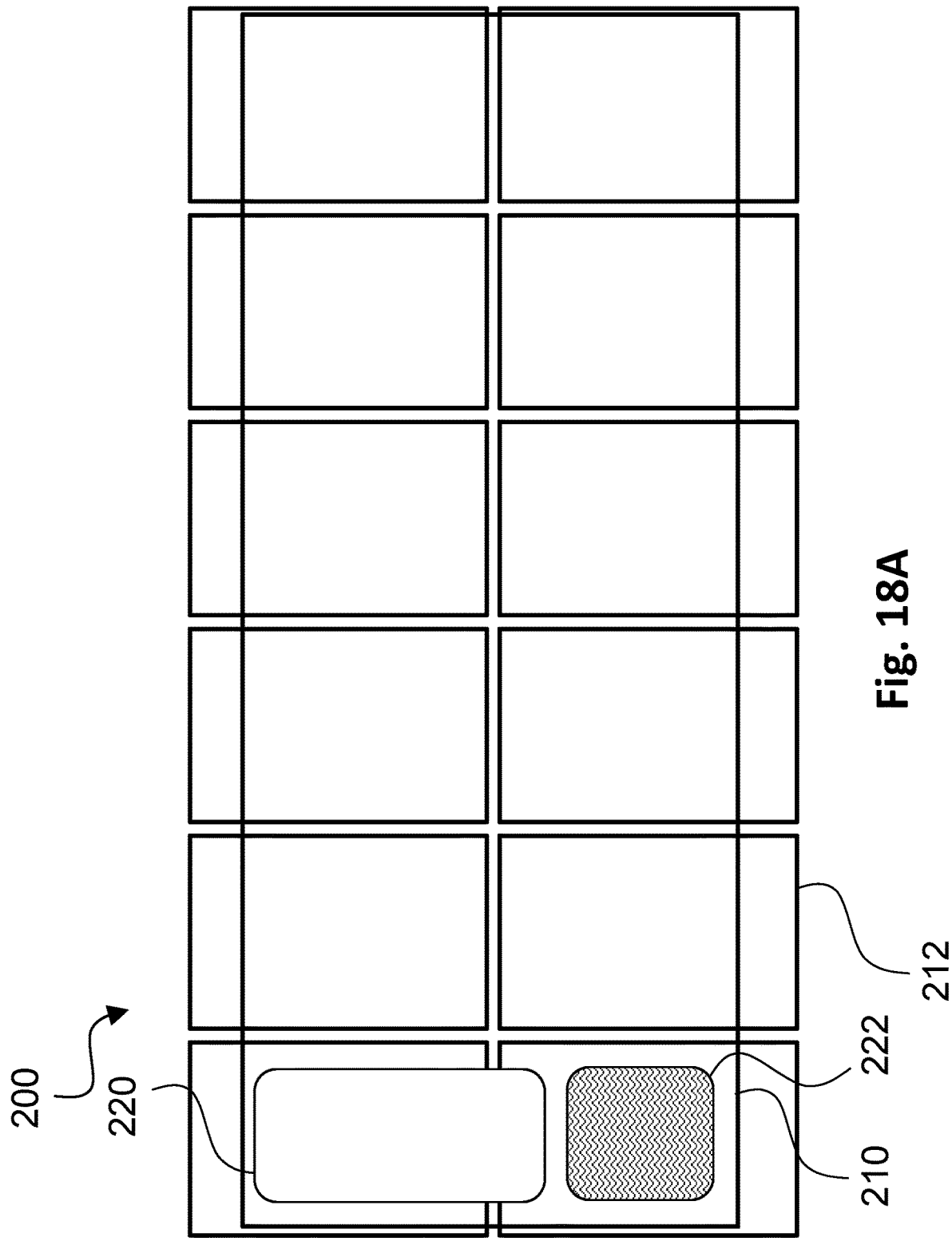
Figure 18B:
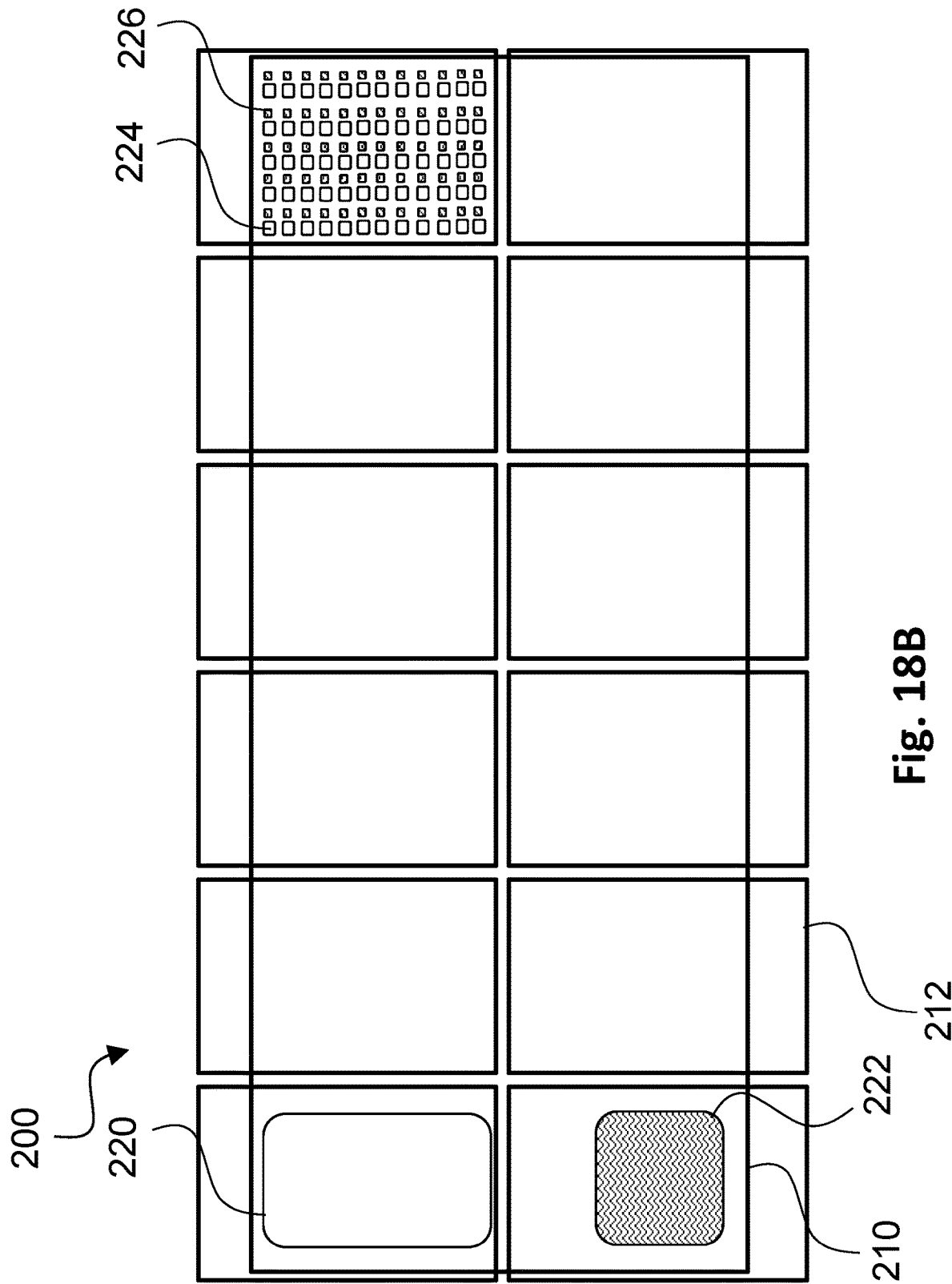

In another aspect of the invention, the digital biological assay may be initiated by merging and mixing of two partitions to form a partition with all the reagents for a biological reaction to take place. FIGS. 18A-18C are drawings depicting a progression of steps constituting another exemplary method of performing a partitioning process to generate partitions for use in a biological assay reaction protocol, in accordance with this embodiment of the present invention. Similarly as to FIG. 12G, FIG. 18A depicts the EWOD cartridge 200 including the array area 210 that contains the array elements of the EWOD device, which is mounted adjacent to the plurality of thermal control elements 212. FIG. 18A depicts two fluid reservoirs, including a biological sample reservoir 220 including the biological entities, and a reagent reservoir 222 containing the reagents needed to start the biological process that initiates the assay but does not contain biological entities.

FIG. 18B shows the initial partitioning of the two reservoirs. In particular, partitions are prepared of both components using methods comparably as described with respect to FIGS. 12B-12F, resulting in the separation of partitions 224 that are dispensed from the biological sample reservoir 220, and partitions 226 that are dispensed from the reagent reservoir 222. The partitions 224 and 226 will have a limited volume variation in accordance with the partitioning process described with respect to FIGS. 12B-12F. As illustrated in FIG. 18C, electrowetting operations then are employed to mix each partition 224 with a corresponding partition 226 to form assay partitions 228. On mixing, the resultant assay partitions 228 contain all the components needed for the biological digital assay of interest, with the mixing initiating the biological processes by introducing the reagents from the reservoir 222 into partitions from the sample reservoir 220. The digital biological assay is then performed as described with respect to previous embodiments.

An aspect of the invention, therefore, is an enhanced electrowetting on dielectric (EWOD) device and a related method of performing a digital biological assay in an EWOD device. In exemplary embodiments, the method of performing a digital biological assay may include the steps of: inputting a sample reservoir containing biological entities and assay reagents into the EWOD device; partitioning the sample reservoir into partitions for the digital biological assay by performing electrowetting operations with the EWOD device; measuring a volume of each partition; changing a condition of the partitions to initiate the digital biological assay, wherein the changed condition results in the biological entities performing a biological process to generate a product substance; and performing the digital biological assay by the steps of: measuring a partition property and a volume of each partition in real time, wherein the partition property is indicative of the product substance generated by the biological process of any biological entity or entities within a respective partition; determining a concentration of the product substance in each partition based on the measured partition property and volume; and categorizing the partitions by a number of biological entities contained in each partition based on the determined concentration of the product substance. The method may include one or more of the following features, either individually or in combination.

In an exemplary embodiment of the method of performing a digital biological assay, the EWOD device includes integrated impedance sensing circuitry, and the volume of each partition is determined based on an impedance sensed by the impedance sensing circuitry.

In an exemplary embodiment of the method of performing a digital biological assay, the partition property comprises an optical property that is measured by an optical sensor of the EWOD device.

In an exemplary embodiment of the method of performing a digital biological assay, the optical property is fluorescence or absorption of the partition of light from a light source that emits light onto the EWOD device.

In an exemplary embodiment of the method of performing a digital biological assay, changing a condition of the partitions to initiate the biological assay comprises at least one of a change in temperature, an addition of an extra chemical component, light activation, or electrochemical activation.

In an exemplary embodiment of the method of performing a digital biological assay, the method further includes plotting time dependent changes in the partition property to determine relative concentrations of the product substance in each partition, and counting the number of biological entities in each partition.

In an exemplary embodiment of the method of performing a digital biological assay, categorizing the partitions comprises deeming partitions that show no change in the partition property as having zero biological entities; deeming those partitions with a slowest rate of increase of the partition property as having one biological entity; deeming those partitions with a next slowest rate of increase of the partition property as having two biological entities; deeming those partitions with a next slowest rate of increase of the partition property as having three biological entities; and deeming those partitions with a next slowest rate of increase of the partition property as having four or more biological entities.

In an exemplary embodiment of the method of performing a digital biological assay, the method further includes estimating an initial concentration of the biological entities in the sample reservoir.

In an exemplary embodiment of the method of performing a digital biological assay, the method further includes determining when a rate of partitions reaching a threshold value of the partition property falls to zero, and categorizing the partitions after the rate of partitions reaching the threshold value of the partition property falls to zero.

In an exemplary embodiment of the method of performing a digital biological assay, the method further includes recording a partition history for each partition comprising a volume of the sample reservoir from which the partitions were generated, an order in which the partitions were generated from the sample reservoir, and the volume of each partition over time.

In an exemplary embodiment of the method of performing a digital biological assay, partitioning the sample reservoir comprises performing at least one iteration of a partitioning process until a sufficient portion of the sample reservoir is partitioned, wherein each iteration comprises: performing an electrowetting operation to pull a plurality of sample droplets from the sample reservoir; measuring a volume of each sample droplet with a sensing system on the EWOD device; calculating a mean droplet volume and setting an acceptable range of variation of droplet volume relative to the mean droplet volume; performing an electrowetting operation to isolate partitions within the acceptable range in an assay area of the EWOD device; and performing an electrowetting operation to merge partitions outside of the acceptable range back into the sample reservoir.

In an exemplary embodiment of the method of performing a digital biological assay, the sensing system comprises integrated impedance sensing circuitry in the EWOD device, and the volume of each sample droplet is determined based on an impedance sensed by the impedance sensing circuitry.

In an exemplary embodiment of the method of performing a digital biological assay, the acceptable range is ±0.5 standard deviations relative to the mean droplet volume.

In an exemplary embodiment of the method of performing a digital biological assay, the acceptable range is ± a percentage relative to the mean droplet volume.

In an exemplary embodiment of the method of performing a digital biological assay, the method comprises performing multiple iterations of the partitioning process.

In an exemplary embodiment of the method of performing a digital biological assay, the method further includes inputting a reagent reservoir containing assay reagents and zero biological entities into the EWOD device; partitioning the reagent reservoir by performing the at least one iteration until a sufficient portion of the reagent reservoir is partitioned; and mixing a partition from the sample reservoir with a corresponding partition of the reagent reservoir to initiate the biological assay.

In an exemplary embodiment of the method of performing a digital biological assay, the biological assay is nucleic acid amplification by polymerase chain reaction (PCR).

In an exemplary embodiment of the method of performing a digital biological assay, the method further includes characterizing a distribution of lengths of nucleic acid molecules in the sample reservoir.

In an exemplary embodiment of the method of performing a digital biological assay, the biological assay comprises one of an enzyme-linked immunosorbent assay (ELISA) for protein biomarker quantitation, an enzymatic assay for quantitation of enzymatic turnover, or a cell-based assay for phenotyping and genotyping.

According to another aspect of the invention, a microfluidic system includes an electro-wetting on dielectric (EWOD) device comprising an element array configured to receive one or more liquid droplets, the element array comprising a plurality of individual array elements; and a control system configured to control actuation voltages applied to the element array to perform manipulation operations to the liquid droplets to perform the method of performing a digital biological assay accordingly to any of the embodiments. The microfluidic system further may include one or more of the following features, either individually or in combination.

In an exemplary embodiment of the microfluidic system, the system further includes a plurality of thermal control elements located at different spatial locations along the EWOD device, at least one of the thermal control elements being variable in temperature with respect to time; wherein the control system includes a thermal control unit configured to control temperatures of the plurality of thermal control elements to generate a plurality of thermal zones located at different spatial locations along the EWOD device.

In an exemplary embodiment of the microfluidic system, the system further includes a light source that emits light onto the array elements, and an optical sensor configured to sense an optical property of liquid droplets dispensed onto the array elements.

In an exemplary embodiment of the microfluidic system, the system further includes integrated impedance sensing circuitry that is integrated into the array elements of the EWOD device, and a volume of liquid droplets dispensed onto the array elements is determined based on an impedance sensed by the impedance sensing circuitry.

Another aspect of the invention is a non-transitory computer-readable medium storing program code which is executed by a processing device for controlling actuation voltages applied to array elements of an element array of an electro-wetting on dielectric (EWOD) device for performing droplet manipulations on droplets on the element array, the program code being executable by the processing device to perform the steps of the method of performing a digital biological assay in an EWOD device accordingly to any of the embodiments.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

INDUSTRIAL APPLICABILITY

The described embodiments could be used to provide enhanced AM-EWOD device operation. The AM-EWOD device can be employed to provide enhanced digital biological assays, such as for example digital polymerase chain reaction (PCR) for nucleic acid quantitation, enzyme-linked immunosorbent assays (ELISA) for protein biomarker quantitation, enzymatic assays for quantitation of enzymatic turnover, and cell-based assays for phenotyping and genotyping. The AM-EWOD device could form a part of a lab-on-a-chip system. Such devices could be used in manipulating, reacting and sensing chemical, biochemical or physiological materials.

What is claimed is:

1. A method of performing a digital biological assay in an electrowetting on dielectric (EWOD) device comprising the steps of:
    inputting a sample reservoir containing biological entities and assay reagents into the EWOD device;
    partitioning the sample reservoir into partitions for the digital biological assay by performing electrowetting operations with the EWOD device;
    measuring a volume of each partition;
    changing a condition of the partitions to initiate the digital biological assay, wherein the changed condition results in the biological entities performing a biological process to generate a product substance; and
    performing the digital biological assay by the steps of:
    measuring a partition property and the volume of each partition in real time, wherein the partition property is indicative of the product substance generated by the biological process of any biological entity or entities within a respective partition;
    determining a concentration of the product substance in each partition by determining a relative concentration of the product substance based on the measured partition property and adjusting the relative concentration based on the measured volume of each partition in real time; and
    categorizing the partitions by a number of biological entities contained in each partition based on the determined concentration of the product substance.

2. The method of claim 1, wherein the EWOD device includes integrated impedance sensing circuitry, and the volume of each partition is determined based on an impedance sensed by the impedance sensing circuitry.

3. The method of claim 1, wherein the partition property comprises an optical property that is measured by an optical sensor of the EWOD device.

4. The method of claim 3, wherein the optical property is fluorescence or absorption of light from a light source that emits the light onto the EWOD device.

5. The method of claim 1, wherein changing the condition of the partitions to initiate the digital biological assay comprises at least one of a change in temperature, an addition of an extra chemical component, light activation, or electrochemical activation.

6. The method of claim 1, further comprising plotting time dependent changes in the partition property to determine relative concentrations of the product substance in each partition, and counting the number of biological entities in each partition.

7. The method of claim 6, further comprising estimating an initial concentration of the biological entities in the sample reservoir.

8. The method of claim 1, wherein categorizing the partitions comprises deeming partitions that show no change in the partition property as having zero biological entities; deeming partitions with a slowest rate of increase of the partition property as having one biological entity; deeming partitions with a next slowest rate of increase of the partition property as having two biological entities; deeming partitions with a next slowest rate of increase of the partition property as having three biological entities; and deeming partitions with a next slowest rate of increase of the partition property as having four or more biological entities.

9. The method of claim 1, further comprising determining when a rate of partitions reaching a threshold value of the partition property falls to zero, and categorizing the partitions after the rate of partitions reaching the threshold value of the partition property falls to zero.

10. The method of claim 1, further comprising recording a partition history comprising a volume of the sample reservoir from which the partitions were generated, an order in which the partitions were generated from the sample reservoir, and the volume of each partition over time.

11. The method of claim 1, wherein partitioning the sample reservoir comprises performing at least one iteration of a partitioning process until a sufficient portion of the sample reservoir is partitioned, wherein each iteration comprises:
    performing the steps of claim 1 of partitioning the sample reservoir into partitions for the digital biological assay by performing electrowetting operations with the EWOD device and measuring the volume of each partition, wherein the volume of each partition is measured with a sensing system on the EWOD device;
    calculating a mean droplet volume and setting an acceptable range of variation of droplet volume relative to the mean droplet volume;
    performing an electrowetting operation to isolate partitions within the acceptable range in an assay area of the EWOD device; and
    performing an electrowetting operation to merge partitions outside of the acceptable range back into the sample reservoir.

12. The method of claim 11, wherein the sensing system comprises integrated impedance sensing circuitry in the EWOD device, and the volume of each sample droplet is determined based on an impedance sensed by the impedance sensing circuitry.

13. The method of claim 11, wherein the acceptable range is ±0.5 standard deviations relative to the mean droplet volume.

14. The method of claim 13, wherein the acceptable range is ± a percentage relative to the mean droplet volume.

15. The method of claim 11, comprising performing multiple iterations of the partitioning process.

16. The method of claim 11, further comprising:
inputting a reagent reservoir containing assay reagents and zero biological entities into the EWOD device;
partitioning the reagent reservoir by performing the at least one iteration until a sufficient portion of the reagent reservoir is partitioned; and
mixing a partition from the sample reservoir with a corresponding partition of the reagent reservoir to initiate the digital biological assay.

17. The method of claim 1, wherein the digital biological assay is nucleic acid amplification by polymerase chain reaction (PCR).

18. The method of claim 17, further comprising characterizing a distribution of lengths of nucleic acid molecules in the sample reservoir.

19. The method of claim 1, wherein the digital biological assay comprises one of an enzyme-linked immunosorbent assay (ELISA) for protein biomarker quantitation, an enzymatic assay for quantitation of enzymatic turnover, or a cell-based assay for phenotyping and genotyping.

20. A microfluidic system comprising:
an electro-wetting on dielectric (EWOD) device comprising an element array configured to receive one or more liquid droplets, the element array comprising a plurality of individual array elements; and
a control system programmed to control actuation voltages applied to the element array to perform the method according to claim 1.

21. The microfluidic system of claim 20, further comprising:
a plurality of thermal control elements located at different spatial locations along the EWOD device, at least one of the plurality of thermal control elements being variable in temperature with respect to time;
wherein the control system includes a thermal control unit configured to control temperatures of the plurality of thermal control elements to generate a plurality of thermal zones located at different spatial locations along the EWOD device.

22. The microfluidic system of claim 20, further comprising a light source that emits light onto the array elements, and an optical sensor configured to sense an optical property of liquid droplets dispensed onto the array elements.

23. The microfluidic system of claim 20, further comprising integrated impedance sensing circuitry that is integrated into the array elements of the EWOD device, and a volume of liquid droplets dispensed onto the array elements is determined based on an impedance sensed by the impedance sensing circuitry.

24. A non-transitory computer-readable medium storing program code which is executed by a processing device for controlling actuation voltages applied to array elements of an element array of an electro-wetting on dielectric (EWOD) device for performing droplet manipulations on droplets on the element array, the program code being executable by the processing device to perform the steps of:
inputting a sample reservoir containing biological entities and assay reagents into the EWOD device;
partitioning the sample reservoir into partitions for a digital biological assay by performing electrowetting operations with the EWOD device;
measuring a volume of each partition;
changing a condition of the partitions to initiate the digital biological assay, wherein the changed condition results in the biological entities performing a biological process to generate a product substance; and
performing the digital biological assay by the steps of:
measuring a partition property and the volume of each partition in real time, wherein the partition property is indicative of the product substance generated by the biological process of any biological entity or entities within a respective partition;
determining a concentration of the product substance in each partition by determining a relative concentration of the product substance based on the measured partition property and adjusting the relative concentration based on the measured volume of each partition in real time; and
categorizing the partitions by a number of biological entities contained in each partition based on the determined concentration of the product substance.

25. The non-transitory computer-readable medium of claim 24, wherein the program code further is executable by the processing device to perform partitioning the sample reservoir by performing at least one iteration of a partitioning process until a sufficient portion of the sample reservoir is partitioned, wherein each iteration comprises:
performing the steps of claim 24 of partitioning the sample reservoir into partitions for the digital biological assay by performing electrowetting operations with the EWOD device and measuring the volume of each partition, wherein the volume of each partition is measured with a sensing system on the EWOD device;
calculating a mean droplet volume and setting an acceptable range of variation of droplet volume relative to the mean droplet volume;
performing an electrowetting operation to isolate partitions within the acceptable range in an assay area of the EWOD device; and
performing an electrowetting operation to merge partitions outside of the acceptable range back into the sample reservoir.

* * * * *